(12) United States Patent
Flohr et al.

(10) Patent No.: US 6,734,179 B2
(45) Date of Patent: May 11, 2004

(54) BENZOTHIAZOLES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/307,698

(22) Filed: Dec. 2, 2002

(65) Prior Publication Data

US 2003/0144288 A1 Jul. 31, 2003

(30) Foreign Application Priority Data

Dec. 12, 2001 (EP) .............................. 01129273

(51) Int. Cl.[7] ................ A61K 31/4436; A61K 31/5377; C07D 413/14; C07D 417/02; C07D 417/14
(52) U.S. Cl. .................... 514/233.8; 514/318; 514/321; 514/338; 514/367; 544/130; 544/131; 544/135; 546/193; 546/198; 546/270.1; 548/163
(58) Field of Search ................. 544/130, 131, 544/135; 546/193, 198, 270.1; 548/163; 514/233.8, 318, 321, 338, 367

(56) References Cited

U.S. PATENT DOCUMENTS

| | | | |
|---|---|---|---|
| 6,521,754 B2 * | 2/2003 | Alanine et al. | 544/129 |
| 6,620,811 B2 * | 9/2003 | Flohr et al. | 514/233.8 |
| 2003/0153566 A1 * | 8/2003 | Flohr et al. | 514/233.8 |

FOREIGN PATENT DOCUMENTS

| | | |
|---|---|---|
| EP | 113219 | 7/1984 |
| EP | 1 116722 | 7/2001 |
| WO | WO 99 24035 | 5/1999 |
| WO | WO 01 97786 | 12/2001 |

OTHER PUBLICATIONS

Poulsen et al., Bioorganic & Medicinal Chemistry, 6, pp. 619–641 (1998).
Müller et al., Bioorganic & Medicinal Chemistry, 6, pp. 707–719 (1998).
Kim et al., J. Med. Chem., 41, pp. 2835–2845 (1998).
Li et al., J. Med. Chem., 41, pp. 3186–3201 (1998).
Baraldi et al., J. Med. Chem., 41, pp. 2126–2133 (1998).
Li et al., J. Med. Chem., 42, pp. 706–721 (1999).
Baraldi et al., J. Med. Chem., 39, pp. 1164–117 (1996).
Colotta et al., Arch. Pharm. Pharm. Med. Chem., 332, pp. 39–41 (1999).
Auchampach et al., Am. J. Physiol., 276, pp. H1113–1116 (1999).
Haas et al., Naunyn Schmiedeberg's Arch. Pharmacol., 362, pp. 375–381 (2000).
Dionisotti et al., Br. J. Pharmacol., 121, pp. 353–360 (1997).

* cited by examiner

Primary Examiner—Fiona T. Powers
(74) Attorney, Agent, or Firm—George W. Johnston; Patricia S. Rocha-Tramaloni; Lyman H. Smith

(57) ABSTRACT

The present invention relates to compounds of the formula

I

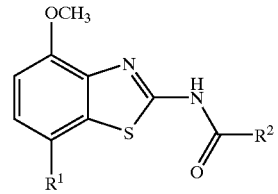

wherein R1 and R2 are as described within. The compounds of formula I have been found to be adenosine receptor ligands. Specifically, the compounds of the present invention have a good affinity to the $A_{2A}$-receptor and they may be used in the treatment of diseases, related to this receptor.

23 Claims, No Drawings

BENZOTHIAZOLES

BACKGROUND OF THE INVENTION

The present invention generally relates to benzothiazole compounds useful as adenosine receptor ligands. Specifically, the present invention relates to compounds having good affinity to the $A_{2A}$-receptor and a high selectivity to the $A_1$- and $A_3$ receptors.

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptores for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtyps has been classically characterised by the adenylate cyclase effector system, which utilises cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtyps is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioural state and (patho)physiological conditions. Under conditions of increased demand and decreased availability of energy (such as hypoxia, hypoglycemia, and/or excessive neuronal activity), adenosine provides a powerful protective fedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_{2a}$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332, 39–41, (1999),
Am. J. Physiol., 276, H1113–1116, (1999) or
Naunyn Schmied, Arch. Pharmacol. 362, 375–381, (2000).

SUMMARY OF THE INVENTION

The present invention relates to compounds of the formula

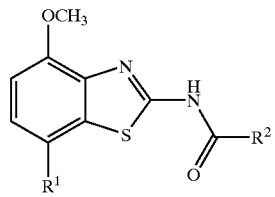

wherein $R^1$ and $R^2$ are as defined herewithin.

The present invention relates to the compounds of formula I per se, the use of compounds of formula I and their pharmaceutically acceptable salts for the manufacture of medicaments for the treatment of diseases related to the adenosine $A_2$ receptor. The present invention further relates to the manufacture of compounds of formula I, medicaments based on these compounds and their production. The present invention also relates to the use of compounds of formula I in the control or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention maybe useful as sedatives, muscle relaxants, antipsychotics, antiepileptics, anticonvulsants and cardiaprotective agents for disorders such as coronary artery disease and heart failure. The most preferred indications in accordance with the present invention are those, which base on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

The present invention relates to compounds of the formula

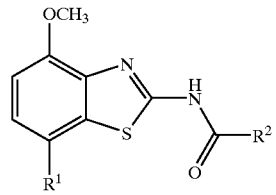

wherein
$R^1$ is 3,6-dihydro-2H-pyran-4-yl, 5,6-dihydro-4H-pyran-3-yl, 5,6-dihydro-4H-pyran-2-yl, tetrahydropyran-2,3 or 4-yl, cyclohex-1-enyl, cyclohexyl, substituted or unsubstituted 1,2,3,6-tetrahydro-pyridin-4-yl or substituted or unsubstituted piperidin-4-yl, wherein when $R^1$ is substituted, the substituent is —C(O)CH$_3$ or —C(O)OCH$_3$ in the 1-position of the N-atom;
$R^2$ is lower alkyl, piperidin-1-yl, piperidin-1-yl substituted by hydroxy, phenyl, phenyl substituted by at least one group selected from the group consisting of —(CH$_2$)$_n$—N(R')—C(O)—(CH$_2$)$_n$—NR'$_2$, —(CH$_2$)$_n$-halogen, lower alkyl and —(CH$_2$)$_n$—N(R')—(CH$_2$)$_n$—O-lower alkyl, morpholinyl, pyridinyl, pyridinyl substituted by at least one group selected from the group consisting of halogen, —N(R')—(CH$_2$)$_n$—O—lower alkyl, lower alkyl, lower alkoxy, morpholinyl and —(CH$_2$)$_n$-pyrrolidinyl;
n is 0, 1 or 2;
R' is hydrogen or lower alkyl;
and pharmaceutically acceptable acid addition salts thereof.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residues is as defined above, and which is attached via an oxygen atom.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present application are compounds of formula I, wherein $R^1$ is 3,6-dihydro-2H-pyran-4-yl, for example the following compound:
[7-(3,6-dihydro-2H-pyran-4-yl)-4-methoxy-benzothiazol-2-yl]-carbamic acid methyl ester.

Further preferred are compounds, wherein $R^1$ is tetrahydropyran-4-yl, for example the following compounds:
4-fluoro-N-[4-methoxy-7-(tetrahydro-pyran-4-yl)-benzothiazol-2-yl]-benzamide,
N-[4-methoxy-7-(tetrahydro-pyran-4-yl)-benzothiazol-2-yl]-6-methyl-nicotinamide, 2-methoxy-N-[4-methoxy-7-(tetrahydro-pyran-4-yl)-benzothiazol-2-yl]-isonicotinamide,
2-ethoxy-N-[4-methoxy-7-(tetrahydro-pyran-4-yl)-benzothiazol-2-yl]-isonicotinamide,
2-ethyl-N-[4-methoxy-7-(tetrahydro-pyran-4-yl)-benzothiazol-2-yl]-isonicotinamide
N-[4-methoxy-7-(tetrahydro-pyran-4-yl)-benzothiazol-2-yl]-2-propyl-isonicotinamide,
2-isopropoxy-N-[4-methoxy-7-(tetrahydro-pyran-4-yl)-benzothiazol-2-yl]-isonicotinamide,
2-isopropyl-N-[4-methoxy-7-(tetrahydro-pyran-4-yl)-benzothiazol-2-yl]-isonicotinamide,
N-[4-methoxy-7-(tetrahydro-pyran-4-yl)-benzothiazol-2-yl]-2-pyrrolidin-1-ylmethyl-isonicotinamide,
morpholine-4-carboxylic acid [4-methoxy-7-(tetrahydro-pyran-4-yl)-benzothiazol-2-yl]-amide,
4-hydroxy-piperidine-1-carboxylic acid [4-methoxy-7-(tetrahydro-pyran-4-yl)-benzothiazol-2-yl]-amide,
2-(2-methoxy-ethylamino)-N-[4-methoxy-7-(tetrahydro-pyran-4-yl)-benzothiazol-2-yl]-isonicotinamide or
2-[(2-methoxy-ethyl)-methyl-amino]-N-[4-methoxy-7-(tetrahydro-pyran-4-yl)-benzothiazol-2-yl]-isonicotinamide.

Further preferred are compounds, wherein $R^1$ is tetrahydropyran-2-yl, for example the following compounds:
2-bromo-N-[4-methoxy-7-(tetrahydro-pyran-2-yl)-benzothiazol-2-yl]-isonicotinamide,
4-fluoro-N-[4-methoxy-7-(tetrahydro-pyran-2-yl)-benzothiazol-2-yl]-benzamide,
N-[4-methoxy-7-(tetrahydro-pyran-2-yl)-benzothiazol-2-yl]-2-methyl-isonicotinamide or
N-[4-methoxy-7-(tetrahydro-pyran-2-yl)-benzothiazol-2-yl]-2-morpholin-4-yl-isonicotinamide A further preferred group of compounds are those, wherein $R^1$ is 1,2,3,6-tetrahydro-pyridin-4-yl, substituted by —C(O)CH$_3$, for example the following compound:
N-[7-(1-acetyl-1,2,3,6-tetrahydro-pyridin-4-yl)-4-methoxy-benzothiazol-2-yl]-4-fluoro-benzamide.

Preferred compounds of the present application are compounds of formula I, wherein $R^1$ is piperidin-4-yl, substituted on the N-atom by —C(O)CH$_3$, for example the following compounds:
N-[7-(1-acetyl-piperidin-4-yl)-4-methoxy-benzothiazol-2-yl]-4-fluoro-benzamide, morpholine-4-carboxylic acid [7-(1-acetyl-piperidin-4-yl)-4-methoxy-benzothiazol-2-yl]-amide,
N-[7-(1-acetyl-piperidin-4-yl)-4-methoxy-benzothiazol-2-yl]-2-methyl-isonicotinamide,
N-[7-(1-acetyl-piperidin-4-yl)-4-methoxy-benzothiazol-2-yl]-4-{[(2-methoxy-ethyl)-methyl-amino-}-benzamide,
N-[7-(1-acetyl-piperidin-4-yl)-4-methoxy-benzothiazol-2-yl]-4-methyl-benzamide,
N-[7-(1-acetyl-piperidin-4-yl)-4-methoxy-benzothiazol-2-yl]-2-morpholin-4-yl-isonicotinamide or
N-[7-(1-acetyl-piperidin-4-yl)-4-methoxy-benzothiazol-2-yl]-2-methoxy-isonicotinamide.

A preferred group of compounds of formula I are further those, wherein $R^1$ is cyclohex-1-enyl, for example the following compound
(7-cyclohex-1-enyl-4-methoxy-benzothiazol-2-yl)-carbamic acid methyl ester.

Preferred compounds of the present application are compounds of formula I, wherein $R^1$ is cyclohexyl, for example the following compounds:
N-(7-cyclohexyl-4-methoxy-benzothiazol-2-yl)-4-fluoro-benzamide,
N-(7-cyclohexyl-4-methoxy-benzothiazol-2-yl)-4-{[(2-methoxy-ethyl)-methyl-amino]-methyl}-benzamide or
N-(7-cyclohexyl-4-methoxy-benzothiazol-2-yl)-2-pyrrolidin-1-yl-methyl-isonicotinamide.

The present compounds of formula I and their pharmaceutically acceptable salts can be prepared by methods known in the art, for example, by processes described below, which process comprises a) reacting a compound of formula

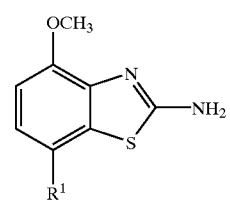

(6)

with a compound of formula

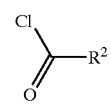

(7)

or with a compound of formula

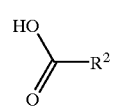

(8)

to a compound of formula

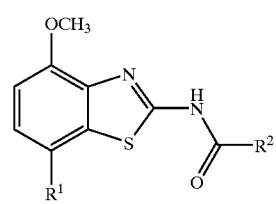

I wherein $R^1$ and $R^2$ are as defined above, or b) hydrogenating a compound of formula

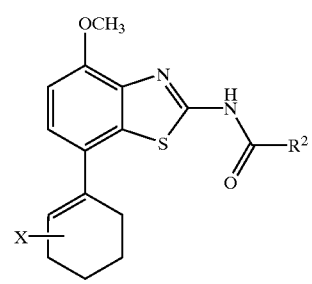

I-4 to a compound of formula

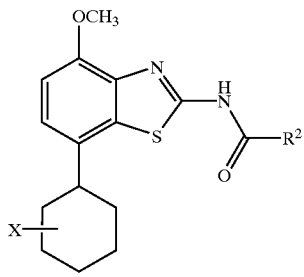

wherein X is a ring atom, selected from the group, consisting of O, N or C, which may be in different ring positions, and wherein the ring N atom may be substituted by —C(O)CH$_3$ or —C(O)OCH$_3$, or c) reacting a compound of formula

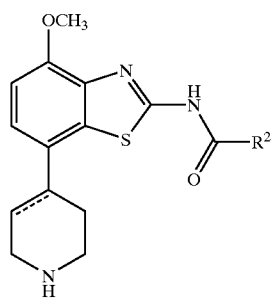

with Ac$_2$O to a compound of formula

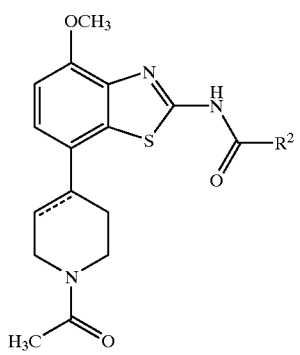

wherein the dotted line may be a bond and R$^2$ is as described above, and if desired, converting the compounds obtained into pharmaceutically acceptable acid addition salts.

The compounds of formula I may be prepared in accordance with process variants a) to c) and with the following schemes 1 to 5.

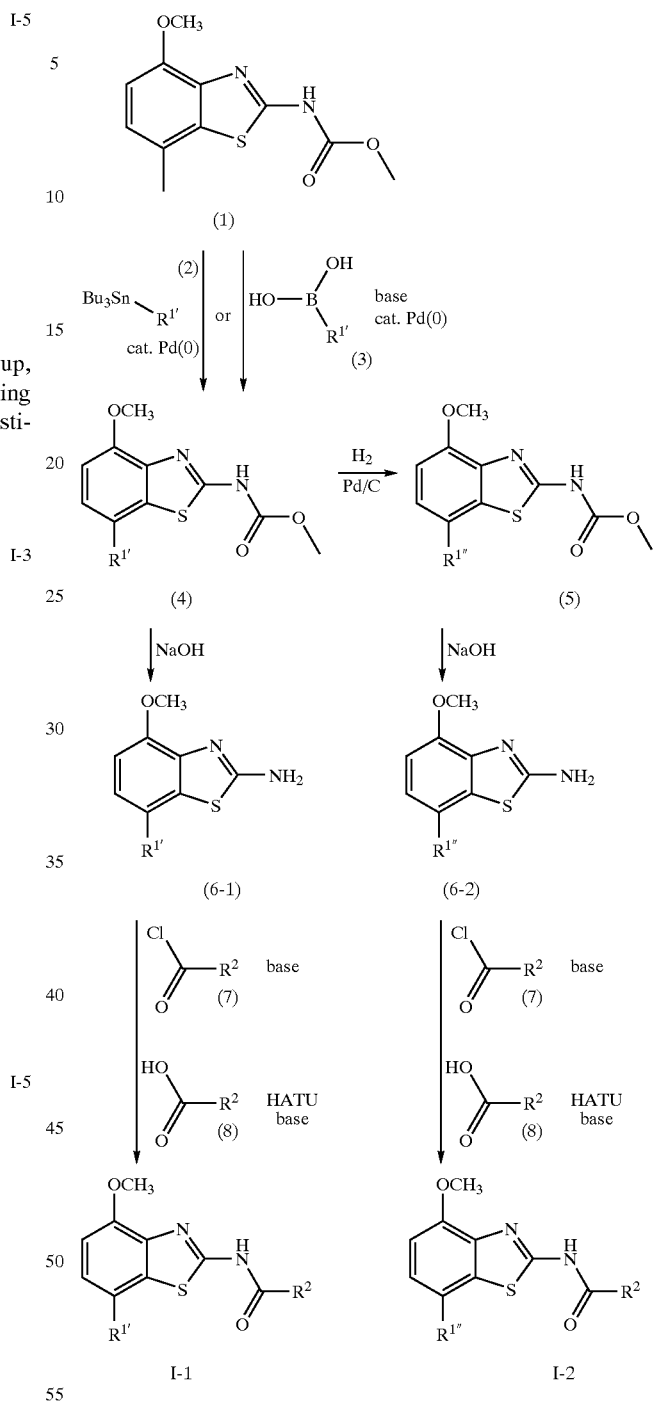

wherein R$^{1'}$ is is 3,6-dihydro-2H-pyran-4-yl, 5,6-dihydro-4H-pyran-3-yl, 5,6-dihydro-4H-pyran-2-yl, cyclohex-1-enyl, or 1,2,3,6-tetrahydro-pyridin-4-yl and and R" is tetrahydropyran-2,3 or 4-yl, cyclohexyl or piperidin-4-yl;

Preparation of Compounds of Formula (4)

The starting 7-iodo-benzothiazole derivatives of formula (1) maybe prepared according to methods disclosed in EP 00113219.0. The starting tributylstannane compounds of formula (2) maybe obtained commercially, for example from Fluka, or may be prepared according to methods well known in the art.

The 7-iodo-benzothiazole derivative of formula (1) is reacted with an excess of a tributylstannane compound of formula (2) in an organic solvent, preferably dioxane, containing a palladium catalyst, preferably bis (dibenzylideneacetone)palladium(0), and a catalytic amount of a phosphine ligand, preferably trifurylphosphine. The reaction is carried out at elevated temperature, preferably about 100° C., for about 2–24 hours, preferably about 16 hours. The product of formula (4) is isolated by conventional means, and preferably purified by means of chromatography or recrystallization.

Alternative Preparation of Compounds of Formula (4)

The starting boronic acid compounds of formula (3) may be obtained commercially, for example from Fluka, or may be prepared according to methods well known in the art.

The compounds of formula (4) may alternatively be prepared by treating 7-iodo-benzothiazole derivatives of formula (1) with an excess of a boronic acid compound of formula (3). The reaction is carried out in an aqueous solvent, preferably a mixture of water and dioxane, containing a palladium catalyst, preferably bis (dibenzylideneacetone)-palladium(0), and a catalytic amount of a phosphine ligand, preferably trifurylphosphine., and an inorganic base, preferably sodium carbonate. The reaction is preferably carried out at the reflux temperature of the solvent, preferably about 100° C., for about 2–24 hours, preferably about 16 hours. The product of formula (4) is isolated by conventional means, and preferably purified by means of chromatography or recrystallization.

Preparation of Compounds of Formula (5)

Compounds of formula (5) may be prepared by hydrogenation of compounds of formula (4) in the presence of a hydrogenation catalyst, preferably 10% palladium on charcoal. These reactions maybe carried out in a variety of organic solvents, such as methanol, ethanol, or tetrahydrofuran, preferably methanol, at room temperature and at a pressure of one atmosphere or above, preferably at one atmosphere, for 16–72 hours, preferably about 72 hours. The product of formula (5) is isolated by conventional means, and preferably purified by means of chromatography or recrystallization.

Preparation of Compounds of Formula (6-1) or (6-2)

One method of preparation of compounds of formula (6-1) or (6-2) is by treatment of a compound of formula (4) or (5) with an excess of sodium hydroxide or potassium hydroxide in an aqueous solvent, preferably aqueous ethylene glycol. The reaction is carried out at elevated temperature, preferably about 100° C., for about 1–16 hours, preferably about 3 hours. The product of formula (6-1) or (6-2) is isolated by conventional means, and preferably purified by means of chromatography or recrystallization.

Preparation of Compounds of Formula I-1 or I-2

One method of preparation of compounds of formula 1 or I-2 is by treatment of a compound of formula (6-1) or (6-2) with a slight excess of an appropriate acyl chloride of formula (7), which may be commercially available or may be prepared by methods well known in the art. The reaction is carried out in a non-protic organic solvent, preferably a mixture of dichloromethane and tetrahydrofuran, containing a base, preferably N-ethyldiisopropylamine or triethylamine, at room temperature for 2–24 hours, preferably 24 hours. The product of formula I is isolated by conventional means, and preferably purified by means of chromatography or recrystallization.

Alternative Preparation of Compounds of formula 1 or I-2

An alternative method of preparation of compounds of formula I involves treatment of an appropriate carboxylic acid of formula (8) with a stoichiometric equivalent of a peptide-coupling reagent, preferably O-(7-azabenzotriazol-1-yl)-N,N,N',N'-tetramethyluronium hexafluorophosphate (HATU), in an ethereal solvent, preferably tetrahydrofuran, containing a base, preferably N-ethyldiisopropylamine, at room temperature for 30–90 minutes, preferably 1 hour. This mixture is then treated with a compound of formula (6) in a solvent mixture, preferably a mixture of tetrahydrofuran, dioxane and N,N-dimethylformamide, at room temperature for 16–24 hours, preferably 16 hours. The product of Formula I is isolated by conventional means, and preferably purified by means of chromatography or recrystallization.

Alternative Preparation of Compounds of Formula (6-2)

An alternative method of preparation of compounds of formula (6-2) is from intermediates of formula (13), the preparation of which is shown in reaction scheme 2 below.

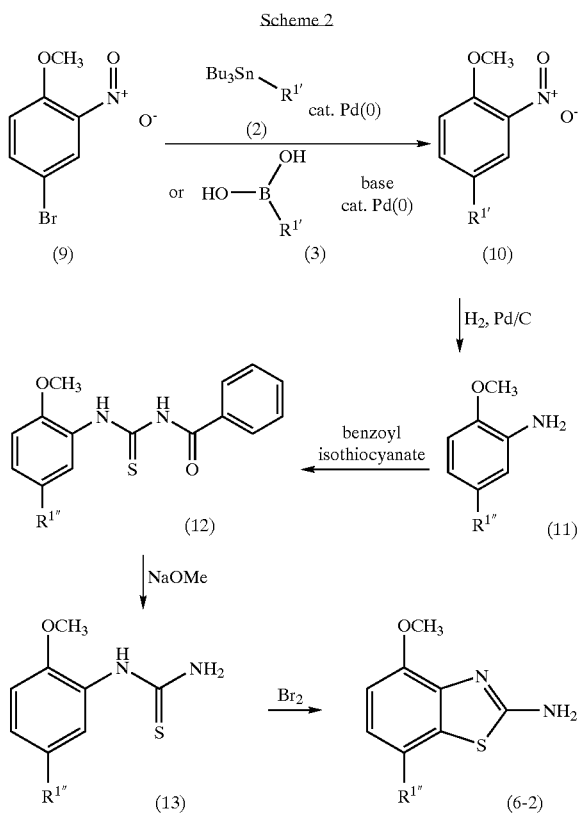

wherein $R^{1'}$ and $R^{1''}$ is as defined for scheme 1.

Preparation of Compounds of Formula (10)

The starting aryl bromide compounds of formula (9) may be obtained commercially, for example from Fluka, or may be prepared according to methods well known in the art. The starting tributylstannane compounds of formula (2) may be obtained commercially, for example from Fluka, or may be prepared according to methods well known in the art.

The aryl bromide compound of formula (9) is reacted with an excess of a tributylstannane compound of formula (2) in an organic solvent, preferably dioxane, containing a palladium catalyst, preferably bis(dibenzylideneacetone) palladium(0), and a catalytic amount of a phosphine ligand, preferably trifurylphosphine. The reaction is carried out at elevated temperature, preferably about 100° C., for about 2–24 hours, preferably about 16 hours. The product of formula (10) is isolated by conventional means, and preferably purified by means of chromatography or recrystallization.

Alternative Preparation of Compounds of Formula (10)

The starting boronic acid compounds of formula (3) may be obtained commercially, for example from Fluka, or may be prepared according to methods well known in the art.

The compounds of formula (10) may alternatively be prepared by treating aryl bromide compounds of formula (9) with an excess of a boronic acid compound of formula (3). The reaction is carried out in an aqueous solvent, preferably a mixture of water and dioxane, containing a palladium catalyst, preferably bis(dibenzylideneacetone)-palladium (0), and a catalytic amount of a phosphine ligand, preferably trifurylphosphine., and an inorganic base, preferably sodium carbonate. The reaction is preferably carried out at the reflux temperature of the solvent, preferably about 100° C., for about 2–24 hours, preferably about 16 hours. The product of formula (10) is isolated by conventional means, and preferably purified by means of chromatography or recrystallization.

Preparation of Compounds of Formula (11)

Compounds of formula (11) may be prepared by hydrogenation of compounds of formula (10) in the presence of a hydrogenation catalyst, preferably 10% palladium on charcoal. These reactions may be carried out in a variety of organic solvents, such as methanol, ethanol, tetrahydrofuran or dichloromethane, preferably a mixture of methanol and dichloromethane, at room temperature and at a pressure of one atmosphere or above, preferably at one atmosphere, for 0.5–16 hours, preferably about 1 hour. The product of formula (11) is isolated by conventional means, and preferably purified by means of chromatography or recrystallization.

Preparation of Compounds of Formula (12)

One method of preparation of compounds of formula (12) involves treatment of a compound of formula (11) with a slight excess of benzoyl isothiocyanate in acetone at a temperature between room temperature and reflux, preferably at room temperature, for 10–30 minutes, preferably 30 minutes. The product of formula (12) is isolated by conventional means, and preferably purified by means of chromatography or recrystallization.

Preparation of Compounds of Formula (13)

A compound of formula (12) is treated with a substoichiometric amount of an alkali metal alcoholate in the corresponding alcohol solvent, preferably sodium methylate in methanol. The reaction is carried out at room temperature for about 0.5–2 hours, preferably about 1 hour. The product of formula (13) is isolated by conventional means, and preferably purified by means of chromatography or rerecrystallization.

Preparation of Compounds of Formula (6-2)

One method of preparation of compounds of formula (6-2) is by treatment of a compound of formula (13) with a stoichiometric equivalent of bromine in a halogenated organic solvent, preferably chloroform. The reaction is carried out at elevated temperature, preferably at the reflux temperature of the solvent, for about 12–18 hours, preferably about 16 hours. The product of formula (6) is isolated by conventional means, and preferably purified by means of chromatography or recrystallization.

Alternative Preparation of Compounds of Formula (10)

An alternative method of preparation of compounds of formula (10) is from an intermediate of formula (14), the preparation of which is shown in reaction scheme 3 below.

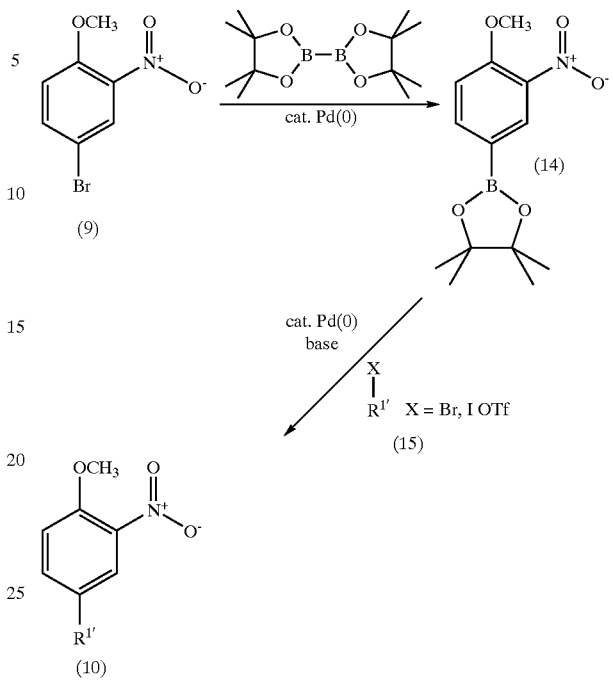

where $R^{1'}$ is as described in scheme 1.

Preparation of Compounds of Formula (14)

The aryl bromide compound of formula (9) is reacted with a slight excess of bis(pinacolato)diboron in an organic solvent, preferably dimethyl sulfoxide, containing a palladium catalyst, preferably dichloro(1,1'-bis (diphenylphosphino)ferrocene)-palladium(II) dichloromethane adduct, and an excess of potassium acetate. The reaction is carried out at elevated temperature) preferably about 80° C., for about 2–24 hours, preferably about 2 hours. The product of formula (14) is isolated by conventional means, and preferably purified by means of chromatography or recrystallization.

Preparation of Compounds of Formula (10)

The starting vinyl bromide, vinyl iodide or vinyl triflate compounds of formula (15) may be obtained commercially, for example from Fluka, or may be prepared according to methods well known in the art.

One method of preparation of compounds of formula (10) is by treatment of a compound of formula (14) with a compound of formula (15) in the presence of a palladium catalyst, preferably dichloro(1,1'-bis(diphenylphosphino) ferrocene)-palladium(II) dichloromethane adduct, and an inorganic base, preferably sodium carbonate. The reaction is carried out in a mixture of solvents, preferably a mixture of ethanol, toluene and water. The reaction is carried out at elevated temperature, preferably about 80° C., for about 0.1–2 hours, preferably about 20 minutes. The product of formula (10) is isolated by conventional means, and preferably purified by means of chromatography or recrystallization.

Scheme 4
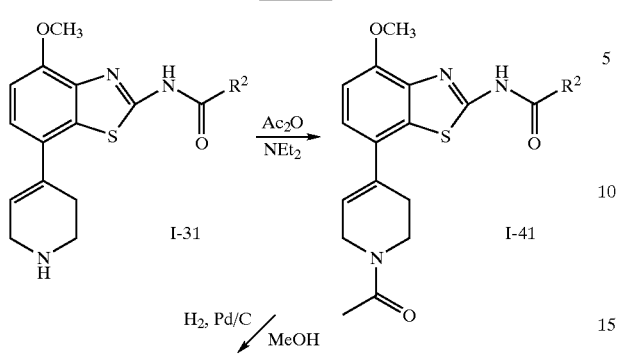
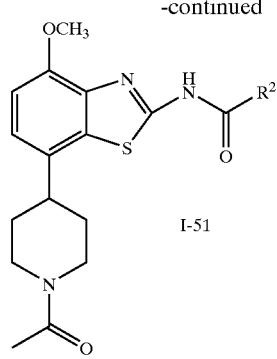
wherein R² is as described above.
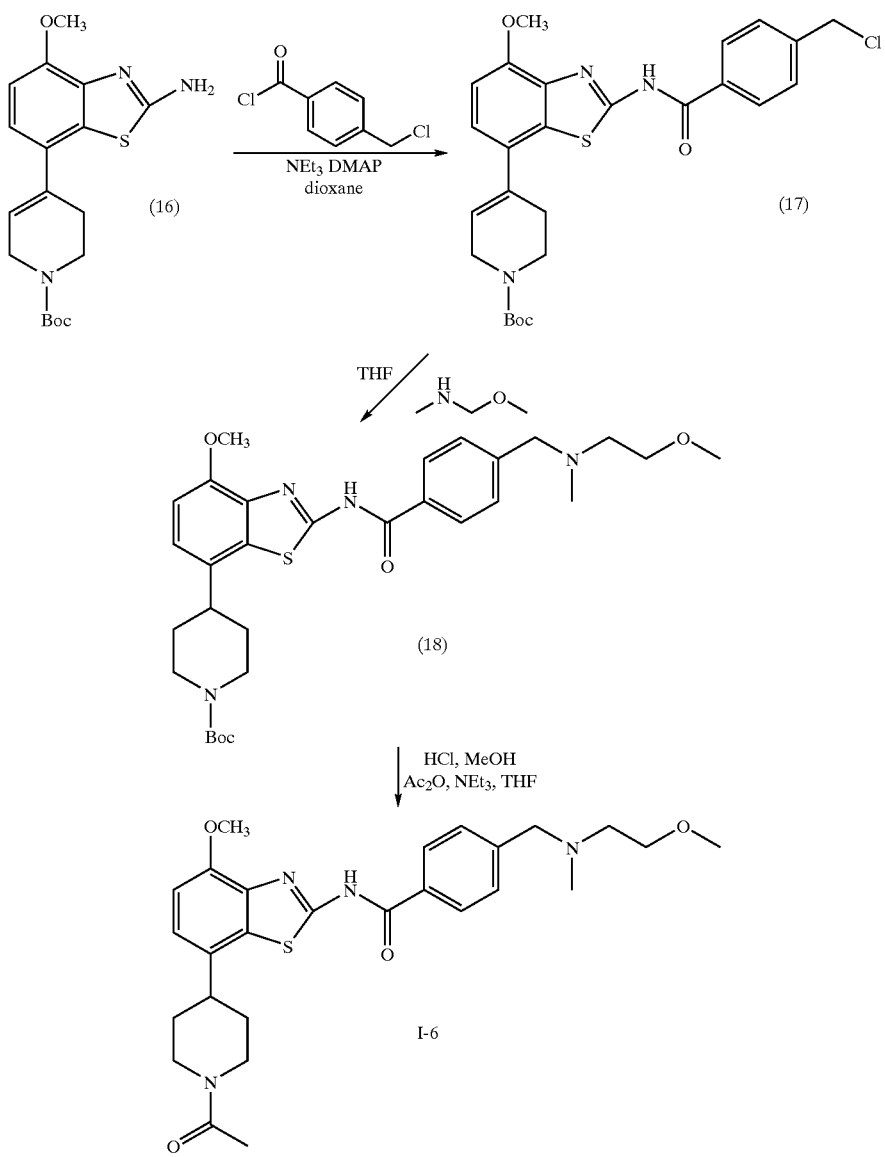

The preparation of compounds described in the above schemes is carried out in conventional manner.

The following abbreviations have been used:
HATU O-(7-azabenzotriazol-1-yl)-N,N,N',N'-tetramethyluronium hexafluorophosphate
DMSO dimethyl sulfoxide
DMAP 4-dimethylaminopyridine
THF tetrahydrofuran Isolation and Purification of the Compounds Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of Formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of Formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands and possess a high affinity towards the adenosine $A_{2A}$ receptor.

The compounds were investigated in accordance with the test given hereinafter.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

The preferred compounds show a pKi>8.0.

| Example No. | $hA_2$ (pKi) |
|---|---|
| 1 | 8.31 |
| 2 | 7.94 |
| 3 | 8.85 |
| 4 | 8.76 |
| 5 | 8.55 |
| 6 | 9.12 |
| 7 | 8.96 |
| 8 | 8.62 |
| 11 | 8.30 |
| 12 | 8.50 |
| 17 | 8.20 |
| 18 | 8.10 |
| 19 | 8.40 |
| 20 | 8.60 |
| 21 | 8.40 |
| 22 | 8.00 |
| 23 | 9.70 |
| 24 | 8.80 |
| 25 | 8.80 |
| 28 | 8.97 |
| 31 | 8.84 |
| 32 | 8.56 |
| 33 | 8.78 |
| 34 | 8.74 |
| 35 | 8.67 |
| 36 | 8.93 |
| 39 | 8.42 |
| 40 | 8.47 |
| 41 | 8.47 |
| 42 | 8.69 |
| 43 | 8.91 |
| 44 | 8.82 |
| 45 | 8.79 |
| 46 | 9.06 |
| 47 | 8.82 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

| | Tablet Formulation (Wet Granulation) | | | | |
|---|---|---|---|---|---|
| | | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | Capsule Formulation | | | | |
|---|---|---|---|---|---|
| | | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

[7-(3,6-Dihydro-2H-pyran-4-yl)-4-methoxy-benzothiazol-2-yl]-carbamic acid methyl ester To a stirred solution of 600 mg (1.65 mmol) (7-iodo-4-methoxy-benzothiazol-2-yl)-carbamic acid methyl ester in 10 ml dioxane were added 1.23 g (3.30 mmol) tri-n-butyl-(3,6-dihydro-2H-pyran-4-yl)-stannane, 28 mg (0.05 mmol) bis(dibenzylideneacetone)palladium and 61 mg (0.26 mmol) trifurylphosphine. The mixture was heated at 100° C. for 16 h and then poured onto water and extracted three times with ethyl acetate. The combined organic phases were dried over sodium sulfate and concentrated in vacuo. Flash chromatography (1/9–1/3 ethyl acetate/hexane) afforded 200 mg [7-(3,6-dihydro-2H-pyran-4-yl)-4-methoxy-benzothiazol-2-yl]-carbamic acid methyl ester as a light brown solid. ES-MS m/e (%): 319 ([M–H], 100).

EXAMPLE 2

[4-Methoxy-7-(tetrahydro-pyran-4-yl)-benzothiazol-2-yl]-carbamic acid methyl ester To a stirred solution of 200 mg (0.62 mmol) [7-(3,6-dihydro-2H-pyran-4-yl)-4-methoxy-benzothiazol-2-yl]-carbamic acid methyl ester in 20 ml methanol was added a spatula end of 10% palladium on charcoal and the mixture was then stirred for 72 h at room temperature under an atmosphere of hydrogen. The mixture was then filtered, washing with dichloromethane, and the filtrate concentrated in vacuo to afford 130 mg (64%) [4-methoxy-7-(tetrahydro-pyran-4-yl)-benzothiazol-2-yl]-carbamic acid methyl ester as an off-white foam. ES-MS m/e (%): 345 (M+Na$^+$, 9), 323 (M+H$^+$, 100).

EXAMPLE 3

4-Fluoro-N-[4-methoxy-7-(tetrahydro-pyran-4-yl)-benzothiazol-2-yl]-benzamide a) 2-(4-Methoxy-3-nitro-phenyl)-4,4,5,5-tetramethyl-[1,3,2]dioxaborolane To a stirred solution of 1.30 g (5.60 mmol) 4-bromo-2-nitroanisole in 25 ml DMSO were added 1.57 g (6.16 mmol) bis(pinacolato)diboron, 123 mg (0.17 mmol) dichloro(1,1'-bis(diphenylphosphino)ferrocene)palladium(II) dichloromethane adduct and 1.65 g (16.8 mmol) potassium acetate. The mixture was heated at 80° C. for 2 h and then cooled to room temperature, poured onto water, and extracted three times with ethyl acetate. The combined organic phases were dried over sodium sulfate and concentrated in vacuo. Flash chromatography (1/2 ethyl acetate/hexane then ethyl acetate) afforded 1.39 g 2-(4-methoxy-3-nitro-phenyl)-4,4,5,5-tetramethyl-[1,3,2]dioxaborolane as an off-white solid. ES-MS m/e (%): 280 (M+H$^+$, 100).

b) 4-(4-Methoxy-3-nitro-phenyl)-3,6-dihydro-2H-pyran

To a stirred solution of 4.36 g (15.6 mmol) 2-(4-methoxy-3-nitro-phenyl)-4,4,5,5-tetramethyl-[1,3,2]dioxaborolane and 3.30 g (14.2 mmol) trifluoromethanesulfonic acid 3,6-dihydro-2H-pyran-4-yl ester in 33 ml ethanol and 82 ml toluene was added 580 mg (0.71 mmol) dichloro(1,1'-bis(diphenylphosphino)ferrocene)palladium(II) dichloromethane adduct. The mixture was heated at 80° C. and 16.5 ml (33.0 mmol) 2 M aqueous sodium carbonate solution was added dropwise. The reaction mixture was stirred for 20 minutes at 80° C. and then cooled to room temperature, poured onto water, and extracted three times with ethyl acetate. The combined organic phases were dried over sodium sulfate and concentrated in vacuo. Flash chromatography (1/4 ethyl acetate/hexane) afforded 2.00 g (60%) 4-(4-methoxy-3-nitro-phenyl)-3,6-dihydro-2H-pyran as a light yellow solid. ES-MS m/e (%): 253 (M+NH$_4$$^+$, 100), 236 (M+H$^+$, 24).

c) 2-Methoxy-5-(tetrahydro-pyran-4-yl)-phenylamine

To a stirred solution of 3.30 g (14.0 mmol) 4-(4-methoxy-3-nitro-phenyl)-3,6-dihydro-2H-pyran in 70 ml methanol and 70 ml dichloromethane was added a spatula end of 10% palladium on charcoal and the mixture was then stirred for 20 minutes at room temperature under an atmosphere of hydrogen. The mixture was then filtered, washing with dichloromethane, and the filtrate concentrated in vacuo to afford 2.75 g (95%) 2-methoxy-5-(tetrahydro-pyran-4-yl)-phenylamine as an off-white crystalline solid. ES-MS m/e (%): 208 (M+H$^+$, 100).

d) 1-Benzoyl-3[-2-methoxy-5-(tetrahydro-pyran-4-yl)-phenyl]-thiourea

To a stirred solution of 2.75 g (13.3 mmol) 2-methoxy-5-(tetrahydro-pyran-4-yl)-phenylamine in 60 ml acetone was added dropwise a solution of 2.04 ml (15.2 mmol) benzoyl isothiocyanate in 30 ml acetone and stirring continued for 30 minutes at room temperature. The mixture was then concentrated in vacuo. Flash chromatography (1/1 ethyl acetate/hexane) followed by trituration in ether afforded 3.25 g (66%) 1-benzoyl-3-[2-methoxy-5-(tetrahydro-pyran-4-yl)-phenyl]-thiourea as a white solid. ES-MS m/e (%): 371 (M+H$^+$, 100).

e) [2-Methoxy-5-(tetrahydro-pyran-4-yl)-phenyl]-thiourea

To a stirred solution of 3.25 g (8.77 mmol) 1-benzoyl-3-[2-methoxy-5-(tetrahydro-pyran-4-yl)-phenyl]-thiourea in 45 ml methanol was added dropwise 0.25 ml (1.32 mmol) 5.3 M sodium methylate solution and stirring continued for 1 h at room temperature. The mixture was then poured onto water and extracted three times with ethyl acetate. The combined organic phases were dried over sodium sulfate and concentrated in vacuo. Flash chromatography (ethyl acetate) afforded 1.90 g (81%) [2-methoxy-5-(tetrahydro-pyran-4-yl)-phenyl]-thiourea as a white foam. ES-MS m/e (%): 267 (M+H$^+$, 100).

f) 4-Methoxy-7-(tetrahydro-pyran-4-yl)-benzothiazol-2-yl-amine

To a stirred solution of 1.90 g (7.13 mmol) [2-methoxy-5-(tetrahydro-pyran-4-yl)-phenyl]-thiourea in 50 ml chloroform was added dropwise 0.37 ml (7.22 mmol) bromine and the mixture heated at reflux for 18 hours. The mixture was then concentrated in vacuo. The residue was recrystallised from ethyl acetate to afford 920 mg (49%) 4-methoxy-7-(tetrahydro-pyran-4-yl)-benzothiazol-2-ylamine as a white solid. ES-MS m/e (%): 265 (M+H$^+$, 100).

g) 4-Fluoro-N-[4-methoxy-7-(tetrahydro-pyran-4-yl)-benzothiazol-2-yl]-benzamide

To a stirred solution of 32 mg (0.23 mmol) 4-fluoro-benzoic acid in 5 ml THF were added 32 mg (0.25 mmol) HATU and 0.043 ml (0.25 mmol) N-ethyldiisopropylamine and stirring continued at room temperature for 1 h. A solution of 60 mg (0.23 mmol) 4-methoxy-7-(tetrahydro-pyran-4-yl)-benzothiazol-2-yl-amine in 5 ml dioxane and 1 ml DMF was then added and stirring continued at room temperature for 16 h. The reaction mixture was then poured into 100 ml water and extracted three times with dichloromethane. The combined organic phases were dried over sodium sulfate and concentrated in vacuo. Flash chromatography (ethyl acetate) followed by trituration in hexane afforded 45 mg (51%) 4-fluoro-N-[4-methoxy-7-(tetrahydro-pyran-4-yl)-benzothiazol-2-yl]-benzamide as a white crystalline solid. ES-MS m/e (%): 387 (M+H$^+$, 100).

In an analogous manner there were obtained:

EXAMPLE 4

2-Bromo-N-[4-methoxy-7-(tetrahydro-pyran-4-yl)-benzothiazol-2-yl]-isonicotinamide From 2-bromo-isonicotinic acid, HATU and N-diethylisopropylamine in THF, then treatment with 4-methoxy-7-(tetrahydro-pyran-4-yl)-benzothiazol-2-ylamine in dioxane and DMF. ES-MS m/e (%): 450 (M{$^{81}$Br}+H$^+$, 100), 448 (M{$^{79}$Br}+H$^+$, 85).

EXAMPLE 5

N-[4-Methoxy-7-(tetrahydro-pyran-4-yl)-benzothiazol-2-yl]-2-methyl-isonicotinamide From 2-methyl-isonicotinic acid hydrochloride, HATU and N-diethylisopropylamine in THF, then treatment with 4-methoxy-7-(tetrahydro-pyran-4-yl)-benzothiazol-2-yl-amine in dioxane and DMF. ES-MS m/e (%): 406 (M+Na$^+$, 46), 384 (M+H$^+$, 100).

EXAMPLE 6

N-[4-Methoxy-7-(tetrahydro-pyran-4-yl)-benzothiazol-2-yl]-2-morpholin-4-yl-isonicotinamide A stirred suspension of 200 mg (0.45 mmol) 2-bromo-N-[4-methoxy-7-(tetrahydro-pyran-4-yl)-benzothiazol-2-yl]-isonicotinamide, 0.39 ml (4.46 mmol) morpholine and 291 mg (0.89 mmol) cesium carbonate in 5 ml N-methylpyrrolidone in a thick-walled glass pressure tube fitted with a teflon cap was heated at 140° C. for 24 h. The reaction mixture was then cooled to room temperature and poured onto water. The mixture was extracted three times with ethyl acetate, and the combined organic phases were washed with saturated brine, dried over sodium sulfate, and concentrated in vacuo. Flash chromatography (1/1 ethyl acetate/hexane) followed by trituration in ether and hexane afforded 90 mg (44%) N-[4-methoxy-7-(tetrahydro-pyran-4-yl)-benzothiazol-2-yl]-2-morpholin-4-yl-isonicotinamide as an off-white crystalline solid. ES-MS m/e (%): 477 (M+Na$^+$, 13),455 (M+H$^+$, 100).

EXAMPLE 7

4-Chloromethyl-N-[4-methoxy-7-(tetrahydro-pyran-4-yl)-benzothiazol-2-yl]-benzamide To a stirred solution of 250 mg (0.95 mmol) 4-methoxy-7-(tetrahydro-pyran-4-yl)-benzothiazol-2-ylamine and 0.95 ml (5.53 mmol) N-ethyldiisopropylamine in 10 ml THF at room temperature was added dropwise a solution of 216 mg (1.14 mmol) 4-(chloromethyl)benzoyl chloride in 3 ml dichloromethane and stirring continued at room temperature for 60 h. The reaction mixture was then concentrated in vacuo. Flash chromatography (1/1 ethyl acetate/hexane) followed by trituration in ether afforded 280 mg (71%) 4-chloromethyl-N-[4-methoxy-7-(tetrahydro-pyran-4-yl)-benzothiazol-2-yl]-benzamide as a white crystalline solid. ES-MS m/e (%): 441 (M$\{^{37}Cl\}$+Na$^+$, 7), 439 (M$\{^{35}Cl\}$+Na$^+$, 21). 419 (M$\{^{37}Cl\}$+H$^+$, 41), 417 (M$\{^{35}Cl\}$+H$^+$, 100).

EXAMPLE 8

4-{[(2-Methoxy-ethyl)-methyl-amino]-methyl}-N-[4-methoxy-7-(tetrahydro-pyran-4-yl)-benzothiazol-2-yl]-benzamide A mixture of 100 mg (0.24 mmol) 4-chloromethyl-N-[4-methoxy-7-(tetrahydro-pyran-4-yl)-benzothiazol-2-yl]-benzamide and 0.21 g (5.53 mmol) N-ethyldiisopropylamine was ultrasonicated at room temperature for 30 minutes. The reaction mixture was then concentrated in vacuo. Flash chromatography (ethyl acetate then 5/95 methanol/ethyl acetate) followed by trituration in ether and hexane afforded 75 mg (67%) 4-{[(2-methoxy-ethyl)-methyl-amino]-methyl}-N-[4-methoxy-7-(tetrahydro-pyran-4-yl)-benzothiazol-2-yl]-benzamide as a white crystalline solid. ES-MS m/e (%): 470 (M+H$^+$, 100).

EXAMPLE 9

[4-Methoxy-7-(1,2,3,6-tetrahydro-pyridin-4-yl)-benzothiazol-2-yl]-carbamic acid methyl ester a) 4-(4-Methoxy-2-methoxycarbonylamino-benzothiazol-7-yl)-3,6-dihydro-2H-pyridine-1-carboxylic acid tert-butyl ester To a stirred solution of 2.2 g (0.006 Mol) (7-iodo-4-methoxy-benzothiazol-2-yl)-carbamic acid methyl ester in 60 ml DMF were added 3.4 g (0.007 Mol) 4-tributylstannanyl-3,6-dihydro-2H-pyridine-1-carboxylic acid tert-butyl ester, 0.424 g (0.001 Mol) PdCl$_2$(PPh$_3$)$_2$ and 0.12 g (0.001 Mol) CuI. The mixture was heated at 100° C. for 19 h and then concentrated in vacuo. Flash chromatography (ethyl acetate/hexane 1:1) afforded 0.91 g (36%) 4-(4-methoxy-2-methoxycarbonylamino-benzothiazol-7-yl)-3,6-dihydro-2H-pyridine-1-carboxylic acid tert-butyl ester as a light yellow foam. ES-MS m/e (%): 362 ([M+H]$^+$, 100).

b) [4-Methoxy-7-(1,2,3,6-tetrahydro-pyridin-4-yl)-benzothiazol-2-yl]-carbamic acid methyl ester 0.03 g (0.072 mMol) 4-(4-methoxy-2-methoxycarbonylamino-benzothiazol-7-yl)-3,6-dihydro-2H-pyridine-1-carboxylic acid tert-butyl ester were dissolved in 0.75 ml 2.5 M HCl/MeOH and heated to reflux for 1.5 h. The reaction mixture was concentrated in vacuo, taken up in 3 ml water and the pH was adjusted to 8 with sat. aqueous sodium bicarbonate. The suspension formed was filtered and the material on the filter was washed with water and dried in vacuo. The residue was subjected to column chromatography (dichloro methane/methanol 9:1+1% NH$_4$OH) to yield 4 mg (18%) [4-methoxy-7-(1,2,3,6-tetrahydro-pyridin-4-yl)-benzothiazol-2-yl]-carbamic acid methyl ester as a beige solid. ES-MS m/e (%): 320 ([M+H]$^+$, 100).

EXAMPLE 10

4-Fluoro-N-[4-methoxy-7-(1,2,3,6-tetrahydro-pyridin-4-yl)-benzothiazol-2-yl]-benzamide Hydrochloride (1:1)

a) 4-(2-Amino-4-methoxy-benzothiazol-7-yl)-3,6-dihydro-2H-pyridine-1-carboxylic acid tert-butyl ester 0.9 g (0.002 Mol) 4-(4-methoxy-2-methoxycarbonylamino-benzothiazol-7-yl)-3,6-dihydro-2H-pyridine-1-carboxylic acid tert-butyl ester were dissolved in a mixture of 7 ml dioxane, 14 ml ethylene glycol and 14 ml 2 N NaOH and heated to 100° C. for 15 h. After cooling to room temperature the pH was adjusted to 7 with 1 N HCl. A precipitation formed, which was filtered, washed with water and dried in vacuo to yield 0.65 g (84%) 4-(2-amino-4-methoxy-benzothiazol-7-yl)-3,6-dihydro-2H-pyridine-1-carboxylic acid tert-butyl ester as a light yellow solid; F.p.: 191–196° C.

b) 4-[2-(4-Fluoro-benzoylamino)-4-methoxy-benzothiazol-7-yl]-3,6-dihydro-2H-pyridine-1-carboxylic acid tert-butyl ester To a solution of 0.25 g (0.69 mMol) 4-(2-amino-4-methoxy-benzothiazol-7-yl)-3,6-dihydro-2H-pyridine-1-carboxylic acid tert-butyl ester in 5 ml THF were added 0.37 ml ethyl diisopropyl amine and 1.0 ml (0.83 mMol) 4-fluoro-benzoyl chloride. The reaction mixture was heated to 40° C. for 3 h. Then 1 ml methanol was added. The solvent was evaporated to dryness, the residue taken up in dichloro methane and washed with water and brine. The organic phase was dried over sodium sulfate and evaporated to dryness in vacuo. The residue was subjected to column chromatography (ethyl acetate/hexane 1:1) to yield 0.275 g (82%) of 4-[2-(4-fluoro-benzoylamino)-4-methoxy-benzothiazol-7-yl]-3,6-dihydro-2H-pyridine-1-carboxylic acid tert-butyl ester as an off-white solid; F.p.: 205–211° C.

c) 4-Fluoro-N-[4-methoxy-7-(1,2,3,6-tetrahydro-pyridin-4-yl)-benzothiazol-2-yl]-benzamide Hydrochloride (1:1)

0.20 g (0.52 mMol) 4-[2-(4-fluoro-benzoylamino)-4-methoxy-benzothiazol-7-yl]-3,6-dihydro-2H-pyridine-1-carboxylic acid tert-butyl ester were dissolved in 5 ml 2.5 M HCl/MeOH and heated to reflux for 1.5 h. The reaction mixture was concentrated in vacuo and taken up in 4 ml isopropanol. The suspension formed was filtered and the material on the filter was washed with diethyl ether and dried in vacuo. One obtained 200 mg (92%) 4-fluoro-N-[4-methoxy-7-(1,2,3,6-tetrahydro-pyridin-4-yl)-benzothiazol-2-yl]-benzamide hydrochloride (1:1) as an off-white solid. F.p.: 268–275° C.

EXAMPLE 11

N-[7-(1-Acetyl-1,2,3,6-tetrahydro-pyridin-4-yl)-4-methoxy-benzothiazol-2-yl]-4-fluoro-benzamide To a solution of 0.12 g (0.28 mMol) 4-fluoro-N-[4-methoxy-7-(1,2,3,6-tetrahydro-pyridin-4-yl)-benzothiazol-2-yl]-benzamide hydrochloride in 3 ml THF were added 0.043 ml triethyl amine. At 0° C. 0.029 ml (0.31 mMol) acetic anhydride was added dropwise and stirred for 30 min. Then a mixture of 5 ml sat. aqueous sodium bicarbonate and 15 ml water were added. After extracting with four times 25 ml ethyl acetate the combined organic phases were dried over sodium sulfate and concentrated to dryness in vacuo to yield 0.088 g (73%) N-[7-(1-acetyl-1,2,3,6-tetrahydro-pyridin-4-yl)-4-methoxy-benzothiazol-2-yl]-4-fluoro-benzamide as an off-white solid; F.p.: 264–265° C.

EXAMPLE 12

N-[7-(1-Acetyl-piperidin-4-yl)-4-methoxy-benzothiazol-2-yl]-4-fluoro-benzamide

To a solution of 0.04 g (0.94 mMol) of N-[7-(1-acetyl-1,2,3,6-tetrahydro-pyridin-4-yl)-4-methoxy-benzothiazol-2-yl]-4-fluoro-benzamide in 2.0 ml of methanol 10.0 mg of Pd/C (10%) were added. This reaction mixture was hydrogenated at 60° C. for 6 h, then filtered and evaporated to dryness in vacuo to yield 0.021 g (52%) N-[7-(1-acetyl-piperidin-4-yl)-4-methoxy-benzothiazol-2-yl]-4-fluoro-benzamide as a white solid. F.p.: 225–233° C.

EXAMPLE 13

Morpholine-4-carboxylic acid [4-methoxy-7-(1,2,3,6-tetrahydro-pyridin-4-yl)-benzothiazol-2-yl]-amide hydrochloride (1:1)

a) 4-{4-Methoxy-2-[(morpholine-4-carbonyl)-amino]-benzothiazol-7-yl}-3,6-dihydro-2H-pyridine-1-carboxylic acid tert-butyl ester To a suspension of 0.15 g (0.42 mMol) 4-(2-amino-4-methoxy-benzothiazol-7-yl)-3,6-dihydro-2H-pyridine-1-carboxylic acid tert-butyl ester in 5 ml dioxane 44 mg (1.0 mMol) NaH (dispersion in mineral oil 60%) were added and stirred for 1 h at room temperature. Then 0.174 ml (1.24 mMol) triethyl amine and 0.114 ml (1.0 mMol) morpholine-4-carbonyl chloride were added and stirred for 16 h at room temperature. After addition of 10 ml water the mixture was extracted three times with 15 ml ethyl acetate. The combined organic phases were dried over sodium sulfate and concentrated to dryness in vacuo. The residue was subjected to column chromatography (ethyl acetate) to yield 0.135 g (69%) 4-{4-methoxy-2-[(morpholine-4-carbonyl)-amino]-benzothiazol-7-yl}-3,6-dihydro-2H-pyridine-1-carboxylic acid tert-butyl ester as a colorless foam. ES-MS m/e (%): 475 ([M+H]$^+$, 100).

b) Morpholine-4-carboxylic acid [4-methoxy-7-(1,2,3,6-tetrahydro-pyridin-4-yl)-benzothiazol-2-yl]-amide hydrochloride (1:1)

0.130 g (0.27 mMol) 4-{4-methoxy-2-[(morpholine-4-carbonyl)-amino]-benzothiazol-7-yl}-3,6-dihydro-2H-pyridine-1-carboxylic acid tert-butyl ester were dissolved in 3 ml 2.5 M HCl/MeOH and heated to reflux for 1.5 h. The reaction mixture was concentrated in vacuo and taken up in 3 ml isopropanol. The suspension formed was filtered and the material on the filter was washed with diethyl ether and dried in vacuo. One obtained 95 mg (84%) morpholine-4-carboxylic acid [4-methoxy-7-(1,2,3,6-tetrahydro-pyridin-4-yl)-benzothiazol-2-yl]-amide hydrochloride (1:1) as an off-white solid. ES-MS m/e (%): 375 ([M+H]$^+$, 100).

EXAMPLE 14

Morpholine-4-carboxylic acid [7-(1-acetyl-1,2,3,6-tetrahydro-pyridin-4-yl)-4-methoxy-benzothiazol-2-yl]-amide To a solution of 0.04 g (0.097 mMol) morpholine-4-carboxylic acid [4-methoxy-7-(1,2,3,6-tetrahydro-pyridin-4-yl)-benzothiazol-2-yl]-amide hydrochloride in 2 ml THF were added 0.016 ml triethyl amine. At 0° C. 0.01 ml (0.11 mMol) acetic anhydride was added dropwise and stirred for 30 min. Then a mixture of 5 ml sat. aqueous sodium bicarbonate and 10 ml water were added. After extracting four times with 15 ml ethyl acetate the combined organic phases were dried over sodium sulfate and concentrated to dryness in vacuo to yield 0.031 g (76%) morpholine-4-carboxylic acid [7-(1-acetyl-1,2,3,6-tetrahydro-pyridin-4-yl)-4-methoxy-benzothiazol-2-yl]-amide as a white solid. ES-MS m/e (%): 417 ([M+H]$^+$, 100).

EXAMPLE 15

Morpholine-4-carboxylic acid [7-(1-acetyl-piperidin-4-yl)-4-methoxy-benzothiazol-2-yl]-amide To a solution of 0.03 g (0.72 mmol) of morpholine-4-carboxylic acid [7-(1-acetyl-1,2,3,6-tetrahydro-pyridin-4-yl)-4-methoxy-benzothiazol-2-yl]-amide in 2.0 ml of methanol 10.0 mg of Pd/C (10%) were added. The reaction mixture was hydrogenated at 60° C. for 6 h, then filtered and evaporated to dryness in vacuo to yield 0.024 g (80%) morpholine-4-carboxylic acid [7-(1-acetyl-piperidin-4-yl)-4-methoxy-benzothiazol-2-yl]-amide as a white solid. F.p.: 196° C. (dec.).

EXAMPLE 16

4-Fluoro-N-(4-methoxy-7-piperidin-4-yl-benzothiazol-2-yl)-benzamide hydrochloride (1:1)

a) 4-[2-(4-Fluoro-benzoylamino)-4-methoxy-benzothiazol-7-yl]-piperidine-1-carboxylic acid tert-butyl ester To a solution of 0.14 g (0.94 mmol) of 4-[2-(4-fluoro-benzoylamino)-4-methoxy-benzothiazol-7-yl]-3,6-dihydro-2H-pyridine-1-carboxylic acid tert-butyl ester in 6.0 ml of methanol and 6.0 ml THF 90.0 mg of Pd/C (10%) were added. The reaction mixture was hydrogenated at 60° C. for 4 h, then filtered and evaporated to dryness in vacuo. The residue was crystallized from diethyl ether to yield 0.105 g (75%) 4-[2-(4-fluoro-benzoylamino)-4-methoxy-benzothiazol-7-yl]-piperidine-1-carboxylic acid tert-butyl ester as a white solid. F.p.: 222–223° C.

b) 4-Fluoro-N-(4-methoxy-7-piperidin-4-yl-benzothiazol-2-yl)-benzamide hydrochloride (1:1)

0.90 g (0.185 mMol) 4-[2-(4-fluoro-benzoylamino)-4-methoxy-benzothiazol-7-yl]-piperidine-1-carboxylic acid tert-butyl ester were dissolved in 3 ml 2.5 M HCl/MeOH and heated to reflux for 1.5 h. The reaction mixture was concentrated in vacuo and taken up in 4 ml isopropanol. The suspension formed was filtered and the material on the filter was washed with diethyl ether and dried in vacuo. One obtained 55 mg (70%) 4-fluoro-N-[4-methoxy-7-piperidine-4-yl-benzothiazol-2-yl]-benzamide hydrochloride (1:1) as a white solid. F.p.: 310–312° C.

EXAMPLE 17

N-[7-(1-Acetyl-piperidin-4-yl)-4-methoxy-benzothiazol-2-yl]-2-methyl-isonicotinamide a) 4-{4-Methoxy-2-[(2-methyl-pyridine-4-carbonyl)-amino]-benzothiazol-7-yl}-3,6-dihydro-2H-pyridine-1-carboxylic acid tert-butyl ester To a solution of 0.35 g (0.97 mMol) 4-(2-amino-4-methoxy-benzothiazol-7-yl)-3,6-dihydro-2H-pyridine-1-carboxylic acid tert-butyl ester in 20 ml THF were added 0.365 ml ethyl diisopropyl amine and 0.2 g (1.10 mMol) 4-(2-chloromethyl)-isonicotinic acid chloride, dissolved in 10 ml dichloro methane. The reaction mixture was stirred at room temperature for 72 h. Then 5 ml methanol were added. The solvent was evaporated to dryness, the residue taken up in dichloro methane and washed with water and brine. The organic phase was dried over sodium sulfate and evaporated to dryness in vacuo. The residue was subjected to column chromatography (ethyl acetate) to yield 0.32 g (69%) of 4-{4-methoxy-2-[(2-methyl-pyridine-4-carbonyl)-amino]-benzothiazol-7-yl}-3,6-dihydro-2H-pyridine-1-carboxylic acid tert-butyl ester as a dark brown solid. ES-MS m/e (%): 481 ([M+H]$^+$, 100).

b) 4-{4-Methoxy-2-[(2-methyl-pyridine-4-carbonyl)-amino]-benzothiazol-7-yl}-piperidine-1-carboxylic acid tert-butyl ester To a solution of 0.30 g (0.62 mMol) of 4-{4-methoxy-2-[(2-methyl-pyridine-4-carbonyl)-amino]-benzothiazol-7-yl}-3,6-dihydro-2H-pyridine-1-carboxylic acid tert-butyl ester in 15.0 ml of methanol and 15.0 ml THF 160.0 mg of Pd/C (10%) were added. The reaction mixture was hydrogenated at 60° C. for 10 h, then filtered and evaporated to dryness in vacuo. The residue was triturated in diethyl ether to yield 0.15 g (53%) 4-{4-methoxy-2-[(2-methyl-pyridine-4-carbonyl)-amino]-benzothiazol-7-yl}-piperidine-1-carboxylic acid tert-butyl ester as a white solid. F.p.: 155–157° C.

c) N-(4-Methoxy-7-piperidin-4-yl-benzothiazol-2-yl)-2-methyl-isonicotinamide hydrochloride (1:2)

0.15 g (0.31 mMol) 4-{4-methoxy-2-[(2-methyl-pyridine-4-carbonyl)-amino]-benzothiazol-7-yl}-piperidine-1-carboxylic acid tert-butyl ester were dissolved in 4 ml 2.5 M HCl/MeOH and heated to reflux for 1.5 h. The reaction mixture was concentrated in vacuo and taken up in 5 ml isopropanol. The suspension formed was filtered and the material on the filter was washed with diethyl ether and dried in vacuo. One obtained 80 mg (57%) N-(4-methoxy-7-piperidin-4-yl-benzothiazol-2-yl)-2-methyl-isonicotinamide hydrochloride (1:2) as a white solid. F.p.: 272–277° C.

d) N-[7-(1-Acetyl-piperidin-4-yl)-4-methoxy-benzothiazol-2-yl]-2-methyl-isonicotinamide To a solution of 0.75 g (0.165 mMol) N-(4-methoxy-7-piperidin-4-yl-benzothiazol-2-yl)-2-methyl-isonicotinamide hydrochloride (1:2) in 4 ml THF were added 0.05 ml triethyl amine. At 0° C. 0.019 ml (0.2 mMol) acetic anhydride was added dropwise and stirred for 1 h. Then a mixture of 5 ml sat. aqueous sodium bicarbonate and 10 ml water were added. A precipitation formed, which was filtered. The residue on the filter was triturated in water. Upon isolation and drying in vacuo one obtained 0.052 g (74%) N-[7-(1-acetyl-piperidin-4-yl)-4-methoxy-benzothiazol-2-yl]-2-methyl-isonicotinamide as a white solid. F.p.: 213–215° C.

EXAMPLES 18+19

N-[7-(1-Acetyl-piperidin-4-yl)-4-methoxy-benzothiazol-2-yl]-4-{[(2-methoxy-ethyl)-methyl amino]-methyl}-benzamide N-[7-(1-Acetyl-piperidin-4-yl)-4-methoxy-benzothiazol-2-yl]-4-methyl-benzamide a) 4-[2-(4-Chloromethyl-benzoylamino)-4-methoxy-benzothiazol-7-yl]-3,6-dihydro-2H-pyridine-1-carboxylic acid tert-butyl ester To a solution of 0.35 g (0.97 mMol) 4-(2-amino-4-methoxy-benzothiazol-7-yl)-3,6-dihydro-2H-pyridine-1-carboxylic acid tert-butyl ester in 20 ml dioxane were added 0.2 ml triethyl amine, 12 mg DMAP and 0.238 g (1.26 mMol) 4-chloromethyl-benzoyl chloride, dissolved in 1 ml of dioxane. The reaction mixture was heated to reflux for 3 h. Then 5 ml methanol were added. The solvent was evaporated to dryness, the residue taken up in ethyl acetate and washed with water and brine. The organic phase was dried over sodium sulfate and evaporated to dryness in vacuo. The residue was subjected to column chromatography (ethyl acetate/hexane 1:1) to yield 0.37, (74%) 4-[2-(4-chloromethyl-benzoylamino)-4-methoxy-benzothiazol-7-yl]-3,6-dihydro-2H-pyridine-1-carboxylic acid tert-butyl ester as a white foam. ES-MS m/e (%): 514 ([M+H]$^+$, 100).

b) 4-[4-Methoxy-2-(4-{[(2-methoxy-ethyl))-methyl-amino]-methyl}-benzoylamino)-benzothiazol-7-yl]-3,6-dihydro-2H-pyridine-1-carboxylic acid tert-butyl ester To a solution of 0.30 g (0.58 mMol) 4-[2-(4-chloromethyl-benzoylamino)-4-methoxy-benzothiazol-7-yl]-3,6-dihydro-2H-pyridine-1-carboxylic acid tert-butyl ester in 10 ml THF were added 0.16 g (1.75 mMol) N-(2-methoxyethyl)-methyl amine. The reaction mixture was heated to 70° C. for 5 h. The solvent was evaporated to dryness, the residue taken up in ethyl acetate and washed with water and brine. The organic phase was dried over sodium sulfate and evaporated to dryness in vacuo. The residue was subjected to column chromatography (dichloro methane/methanol 19:1) to yield 0.27 g (82%) of 4-[4-methoxy-2-(4-{[(2-methoxy-ethyl)-methyl-amino]-methyl}-benzoylamino)-benzothiazol-7-yl]-3,6-dihydro-2H-pyridine-1-carboxylic acid tert-butyl ester as a white foam. ES-MS m/e (%): 567 ([M+H]$^+$, 100).

c) 4-[4-Methoxy-2-(4-[(2-methoxy-ethyl)-methyl-amino]-methyl-benzoylamino)-benzothiazol-7-yl]-piperidine-1-carboxylic acid tert-butyl ester To a solution of 0.27 g (0.48 mMol) of 4-[4-methoxy-2-(4-{[(2-methoxy-ethyl)-methyl-amino]-methyl}-benzoylamino)-benzothiazol-7-yl]-3,6-dihydro-2H-pyridine-1-carboxylic acid tert-butyl ester in 5.0 ml of methanol and 5.0 ml THF 100 mg of Pd/C (10 %) were added. The reaction mixture was hydrogenated at 60° C. for 10 h, then filtered and evaporated to dryness in vacuo. The residue was triturated in diethyl ether to yield 0.15 g of an inseparable mixture of 4-{4-methoxy-2-[(2-methyl-pyridine-4-carbonyl)-amino]-benzothiazol-7-yl}-piperidine-1-carboxylic acid tert-butyl ester and 4-[2-(4-methyl-benzoylamino)-4-methoxy-benzothiazol-7-yl]-piperidine-1-carboxylic acid tert-butyl ester as a white solid, which was directly used in the next step.

0.14 g of the above mentioned mixture were dissolved in 3 ml 2.5 M HCl/MeOH and heated to reflux for 1.5 h. The reaction mixture was concentrated in vacuo and taken up in 5 ml isopropanol. The suspension formed was filtered and the material on the filter was washed with diethyl ether and dried in vacuo. One obtained 100 mg of a mixture of N-[7-(piperidin-4-yl)-4-methoxy-benzothiazol-2-yl]-4-{[(2-methoxy-ethyl)-methyl-amino]-methyl}-benzamide hydrochloride and N-[7-(piperidin-4-yl)-4-methoxy-benzothiazol-2-yl]-4-methyl-benzamide hydrochloride as a white solid, which was directly used in the next step.

d) N-[7-(1-Acetyl-piperidin-4-yl)-4-methoxy-benzothiazol-2-yl]-4-{[(2-methoxy-ethyl)-methyl-amino]-methyl}-benzamide N-[7-(1-Acetyl-piperidin-4-yl)-4-methoxy-benzothiazol-2-yl]-4-methyl-benzamide To a solution of 0.1 g of the above mentioned mixture in 4 ml THF were added 0.05 ml triethyl amine. At 0° C. 0.02 ml (0.21 mMol) acetic anhydride was added dropwise and stirred for 1 h. Then a mixture of 5 ml sat. aqueous sodium bicarbonate and 10 ml water were added. The aqueous phase was extracted three times with 15 ml ethyl acetate. The combined organic phases were dried over sodium sulfate and concentrated to dryness in vacuo. The residue was subjected to column chromatography (dichloro methane/methanol 19:1) to yield 0.02 g (22%) N-[7-(1-acetyl-piperidin-4-yl)-4-methoxy-benzothiazol-2-yl]-4-{[(2-methoxy-ethyl)-methyl-amino]-methyl}-benzamide as a white solid, F.p.: 175–178° C. and 0.032 g (42%) N-[7-(1-acetyl-piperidin-4-yl)-4-methoxy-benzothiazol-2-yl]-4-methyl-benzamide as a white solid; F.p.: 255–258° C.

EXAMPLE 20

N-[7-(1-Acetyl-piperidin-4-yl)-4-methoxy-benzothiazol-2-yl]-2-morpholin-4-yl-isonicotinamide a) 4-{2-[(2-Chloro-pyridine-4-carbonyl)-amino]-4-methoxy-benzothiazol-7-yl}-3,6-dihydro-2H-pyridine-1-carboxylic acid tert-butyl ester To a solution of 0.25 g (0.69 mMol) 4-(2-amino-4-methoxy-benzothiazol-7-yl)-3,6-dihydro-2H-pyridine-1-carboxylic acid tert-butyl ester in 10 ml THF were added 0.26 ml ethyl diisopropyl amine and 0.16 g (0.76 mMol) 2-chloro-isonicotinoyl chloride, dissolved in 5 ml of dichloro methane. The reaction mixture was stirred at room temperature for 16 h. Then 5 ml methanol were added. The solvent was evaporated to dryness, the residue taken up in ethyl acetate and washed with water and brine. The organic phase was dried over sodium sulfate and evaporated to dryness in vacuo. The residue was subjected to column chromatography (ethyl acetate/hexane 1:1) to yield 0.308 g (89%) of 4-{2-[(2-chloro-pyridine-4-carbonyl)-amino]-4-methoxy-benzothiazol-7-yl}-3,6-dihydro-2H-pyridine-1-carboxylic acid tert-butyl ester as a yellow foam. ES-MS m/e (%): 501 ([M+H]$^+$, 100).

b) 4-{4-Methoxy-2-[(2-morpholin-4-yl-pyridine-4-carbonyl)-amino]-benzothiazol-7-yl}-3,6-dihydro-2H-pyridine-1-carboxylic acid tert-butyl ester 0.30 g (0.60 mMol) 4-{2-[(2-chloro-pyridine-4-carbonyl)-amino]-4-methoxy-benzothiazol-7-yl}-3,6-dihydro-2H-pyridine-1-carboxylic acid tert-butyl ester were heated to 130° C. for 24 h in 1 ml morpholine and 0.39 g (1.2 mMol) cesium carbonate. The morpholin has been removed in vacuo. The residue has been triturated in ethyl acetate and subsequently subjected to column chromatography (ethyl acetate) to yield 0.15 g (45%) 4-{4-methoxy-2-[(2-morpholin-4-yl-pyridine-4-carbonyl)-amino]-benzothiazol-7-yl}-3,6-dihydro-2H-pyridine-1-carboxylic acid tert-butyl ester as a yellow foam. ES-MS m/e (%): 552 ([M+H]$^-$, 100).

c) 4-{4-Methoxy-2-[(2-morpholin-4-yl-pyridine-4-carbonyl)-amino]-benzothiazol-7-yl}-piperidine-1-carboxylic acid tert-butyl ester To a solution of 0.15 g (0.27 mMol) of 4-{4-methoxy-2-[(2-morpholin-4-yl-pyridine-4-carbonyl)-amino]-benzothiazol-7-yl}-3,6-dihydro-2H-pyridine-1-carboxylic acid tert-butyl ester in 6.0 ml of methanol and 6.0 ml THF 50 mg of Pd/C (10%) were added. The reaction mixture was hydrogenated at 60° C. for 6 h, then filtered and evaporated to dryness in vacuo. The residue was subjected to column chromatography (ethyl acetate) to yield 0.083 g (55%) 4-{4-methoxy-2-[(2-morpholin-4-yl-pyridine-4-carbonyl)-amino]-benzothiazol-7-yl}-piperidine-1-carboxylic acid tert-butyl ester as a yellow foam. ES-MS m/e (%): 554 ([M+H]$^+$, 100).

d) N-(4-Methoxy-7-piperidin-4-yl-benzothiazol-2-yl)-2-morpholin-4-yl-isonicotinamide 1:2 Hydrochloride 0.08 g (0.14 mMol) 4-{4-methoxy-2-[(2-morpholin-4-yl-pyridine-4-carbonyl)-amino]-benzothiazol-7-yl}-piperidine-1-carboxylic acid tert-butyl ester were dissolved in 2 ml 2.5 M HCl/MeOH and heated to reflux for 1.5 h. The reaction mixture was concentrated in vacuo and taken up in 3 ml isopropanol. The suspension formed was filtered and the material on the filter was washed with diethyl ether and dried in vacuo. One obtained 54 mg (71%) N-(4-methoxy-7-piperidin-4-yl-benzothiazol-2-yl)-2-morpholin-4-yl-isonicotinamide 1:2 hydrochloride as a yellow solid. F.p.: 260–270° C. (dec.).

e) N-[7-(1-Acetyl-piperidin-4-yl)-4-methoxy-benzothiazol-2-yl]-2-morpholin-4-yl-isonicotinamide To a solution of 0.05 g (0.095 mMol) N-(4-methoxy-7-piperidin-4-yl-benzothiazol-2-yl)-2-morpholin-4-yl-isonicotinamide 1:2 hydrochloride in 3 ml THF were added 0.029 ml triethyl amine. At 0° C. 0.011 ml (0.11 mMol) acetic anhydride was added dropwise and stirred for 1 h. Then a mixture of 5 ml sat. aqueous sodium bicarbonate and 10 ml water were added. This was extracted three times with 15 ml ethyl acetate, the combined organic phase were dried over sodium sulfate and evaporated to dryness in vacuo. One obtained 0.031 g (66%) N-[7-(1-acetyl-piperidin-4-yl)-4-methoxy-benzothiazol-2-yl]-2-morpholin-4-yl-isonicotinamide as a white solid. F.p.: 231–233° C.

EXAMPLE 21

N-[7-(1-Acetyl-piperidin-4-yl)-4-methoxy-benzothiazol-2-yl]-2-methoxy-isonicotinamide a) 4-{2-[(2-Chloro-6-methoxy-pyridine-4-carbonyl)-amino]-4-methoxy-benzothiazol-7-yl}-3,6-dihydro-2H-pyridine-1-carboxylic acid tert-butyl ester To a solution of 0.35 g (0.97 mMol) 4-(2-amino-4-methoxy-benzothiazol-7-yl)-3,6-dihydro-2H-pyridine-1-carboxylic acid tert-butyl ester in 15 ml THF were added 0.33 ml ethyl diisopropyl amine and 0.23 g (0.96 mMol) 2-chloro-6-methoxypyridin-4-carbonic acid chloride, dissolved in 10 ml dichloro methane. The reaction mixture was stirred at room temperature for 72 h. Then 5 ml methanol were added. The solvent was evaporated to dryness, the residue taken up in dichloro methane and washed with water and brine. The organic phase was dried over sodium sulfate and evaporated to dryness in vacuo. The residue was subjected to column chromatography (ethyl acetate/hexane 1:1) to yield 0.404 g (87%) of 4-{2-[(2-chloro-6-methoxy-pyridine-4-carbonyl)-amino]-4-methoxy-benzothiazol-7-yl}-3,6-dihydro-2H-pyridine-1-carboxylic acid tert-butyl ester as a light yellow foam. ES-MS m/e (%): 531 ([M+H]$^+$, 100).

b) 4-{4-Methoxy-2-[(2-methoxy-pyridine-4-carbonyl)-amino]-benzothiazol-7-yl}-piperidine-1-carboxylic acid tert-butyl ester To a solution of 0.39 g (0.73 mMol) of 4-{2-[(2-chloro-6-methoxy-pyridine-4-carbonyl)-amino]-4-methoxy-benzothiazol-7-yl}-3,6-dihydro-2H-pyridine-1-carboxylic acid tert-butyl ester in 16.0 ml of methanol and 16.0 ml THF 100 mg of Pd/C (10%) and 0.15 ml triethyl amine were added. The reaction mixture was hydrogenated at 60° C. for 6 h, then filtered and evaporated to dryness in vacuo. The residue was subjected to column chromatography (ethyl acetate/hexane 1:1) to yield 0.110 g (30%) 4-{4-methoxy-2-[(2-methoxy-pyridine-4-carbonyl)-amino]-benzothiazol-7-yl}-piperidine-1-carboxylic acid tert-butyl ester as a white foam. ES-MS m/e (%): 499 ([M+H]$^+$, 100).

c) 2-Methoxy-N-(4-methoxy-7-piperidin-4-yl-benzothiazol-2-yl)-isonicotinamide 1:2 Hydrochloride 0.10 g (0.20 mMol) 4-{4-methoxy-2-[(2-methoxy-pyridine-4-carbonyl)-amino]-benzothiazol-7-yl}-piperidine-1-carboxylic acid tert-butyl ester were dissolved in 2 ml 2.5 M HCl/MeOH and heated to reflux for 1.5 h. The reaction mixture was concentrated in vacuo and taken up in 3 ml isopropanol. The suspension formed was filtered and the material on the filter was washed with diethyl ether and dried in vacuo. One obtained 0.075 g (86%) 2-methoxy-N-(4-methoxy-7-piperidin-4-yl-benzothiazol-2-yl)-isonicotinamide 1:2 hydrochloride as a yellow solid. F.p.: 305–310° C.

d) N-[7-(1-Acetyl-piperidin-4-yl)-4-methoxy-benzothiazol-2-yl]-2-methoxy-isonicotinamide To a solution of 0.07 g (0.16 mMol) 2-methoxy-N-(4-methoxy-7-piperidin-4-yl-benzothiazol-2-yl)-isonicotinamide 1:2 hydrochloride in 4 ml THF were added 0.049 ml triethyl amine. At 0° C. 0.018 ml (0.11 mMol) acetic anhydride was added dropwise and stirred for 1 h. Then a mixture of 5 ml sat. aqueous sodium bicarbonate and 10 ml water were added. This was extracted three times with 15 ml ethyl acetate, the combined organic phases were dried over sodium sulfate and evaporated to dryness in vacuo. One obtained 0.036 g (51%) N-[7-(1-acetyl-piperidin-4-yl)-4-methoxy-benzothiazol-2-yl]-2-methoxy-isonicotinamide as a white solid. F.p.: 242–244° C.

EXAMPLE 22

(7-Cyclohex-1-enyl-4-methoxy-benzothiazol-2-yl)-carbamic acid methyl ester

To a stirred solution of 100 mg (0.27 mmol) (7-iodo-4-methoxy-benzothiazol-2-yl)-carbamic acid methyl ester in 3 ml dioxane were added 0.2 g (0.54 mmol) tri-n-butyl-(1-cyclohex-1-enyl)-stannane, 5.0 mg (0.009 mmol) bis (dibenzylideneacetone)palladium and 10 mg (0.043 mmol) trifurylphosphine. The mixture was heated at 100° C. for 16 h and then poured onto water and extracted three times with ethyl acetate. The combined organic phases were dried over sodium sulfate and concentrated in vacuo. Flash chromatography (ethyl acetate/hexane 1:4) afforded 16 mg (7-Cyclohex-1-enyl-4-methoxy-benzothiazol-2-yl)-carbamic acid methyl ester (18%) as an off white solid; F.p.: 164–173° C.

EXAMPLE 23

N-(7-Cyclohexyl-4-methoxy-benzothiazol-2-yl)-4-fluoro-benzamide a) 4-Cyclohex-1-enyl-1-methoxy-2-nitro-benzene To a stirred solution of 2.1 g (0.0091 Mol) 4-bromo-2-nitroanisole in 50 ml dioxane were added 1.05 g (0.00091 Mol) tetrakis(triphenylphosphine)palladium, 4.03 g (0.011 Mol) tri-n-butyl-(1-cyclohex-1-enyl)-stannane and 18.3 ml 2 M aqueous $Na_2CO_3$ solution. The mixture was heated for 16 h at reflux and then poured onto water. After extraction with dichloro methane, drying of the combined organic phases over sodium sulfate and evaporation of the solvent the crude material was subjected to column chromatography (ethyl acetate/hexane 1:10) to yield 1.57 g of 4-cyclohex-1-enyl-1-methoxy-2-nitro-benzene as a yellow liquid. EI-MS m/e (%): 233 ([M]$^+$, 100).

b) 5-Cyclohexyl-2-methoxy-phenylamine

To a solution of 0.87 g (0.37 mMol) of 5-cyclohex-1-enyl-1-methoxy-2-nitro-benzene in 2.0 ml of ethanol 3.0 mg of Pd/C (10%) were added. This reaction mixture was hydrogenated at 40° C. for 2 h then filtered and evaporated to dryness in vacuo to yield 0.072 g of 5-cyclohexyl-2-methoxy-phenylamine (90%) as a light brown solid. ES-MS m/e (%): 206 ([M+H]$^+$, 100).

c) (5-Cyclohexyl-2-methoxy-phenyl)-thiourea 1.3 g (0.0063 Mol) 5-cyclohexyl-2-methoxy-phenylamine and 2.45 g (0.0252 Mol) potassium thioisocyanate were dissolved in a mixture of 12 ml water and 2 ml conc. HCl. The reaction mixture was heated to reflux for 16 h and then poured onto a mixture of water and dichloro methane. The aqueous phase was extracted with dichloro methane, washed with brine, dried over sodium sulfate and evaporated in vacuo. The residue was subjected to column chromatography (ethyl acetate/hexane 1:4->1:1) yielding 1.0 g (60%) of (5-cyclohexyl-2-methoxy-phenyl)-thiourea as a yellow foam. ES-MS m/e (%): 265 ([M+H]$^+$, 100).

d) 7-Cyclohexyl-4-methoxy-benzothiazol-2-yl-amine

To a solution of 0.9 g (0.0034 Mol) (5-cyclohexyl-2-methoxy-phenyl)-thiourea in 18 ml chloroform were added 0.2 ml (0.0041 Mol) bromine, dissolved in 4.5 ml chloroform and heated to reflux for 16 h. The reaction mixture was diluted with dichloromethane, extracted with sat. aqueous potassium carbonate and brine, dried over sodium sulfate and evaporated to dryness in vacuo. The residue was crystallized from ethyl acetate/diethyl ether to yield 0.61 g (68%) of 7-cyclohexyl-4-methoxy-benzothiazol-2-ylamine as an off-white solid; F.p.: 199–200° C.

e) N-(7-Cyclohexyl-4-methoxy-benzothiazol-2-yl)-4-fluoro-benzamide

To a solution of 0.05 g (0.19 mMol) 7-cyclohexyl-4-methoxy-benzothiazol-2-ylamine in 2 ml THF were added 0.1 ml ethyl diisopropyl amine and 0.027 ml (0.23 mMol) 4-fluoro-benzoyl chloride. The reaction mixture was heated to 70° C. for 2 h. The solvent was evaporated to dryness, the residue taken up in dichloro methane and washed with water and brine. The organic phase was dried over sodium sulfate and evaporated to dryness in vacuo. The residue was subjected to column chromatography (ethyl acetate/hexane 1:9, 1:4) to yield 0.01 g (14%) of N-(7-cyclohexyl-4-methoxy-benzothiazol-2-yl)-4-fluoro-benzamide as a light yellow solid; F.p.: 192–195° C.

EXAMPLE 24

N-(7-Cyclohexyl-4-methoxy-benzothiazol-2-yl)-4-{[(2-methoxy-ethyl)-methyl-amino]-methyl}-benzamide a) 4-Chloromethyl-N-(7-cyclohexyl-4-methoxy-benzothiazol-2-yl)-benzamide To a solution of 0.1 g (0.38 mMol) 7-cyclohexyl-4-methoxy-benzothiazol-2-ylamine in 3 ml THF were added 0.2 ml ethyl diisopropyl amine and 0.0865 g (0.46 mMol) 4-chloromethyl-benzoyl chloride, dissolved in 1 ml of dichloro methane. The reaction mixture was stirred at room temperature for 16 h. The solvent was evaporated to dryness, the residue taken up in dichloro methane and washed with water and brine. The organic phase was dried over sodium sulfate and evaporated to dryness in vacuo. The residue was triturated in ethyl ether, filtered and dried to yield 0.11 g (68%) of 4-chloromethyl-N-(7-cyclohexyl-4-methoxy-benzothiazol-2-yl)-benzamide as a light yellow foam. ES-MS m/e (%): 415 ([M+H]$^+$, 100).

b) N-(7-Cyclohexyl-4-methoxy-benzothiazol-2-yl)-4-{[(2-methoxy-ethyl)-methyl-amino]-methyl}-benzamide To a solution of 0.095 g (0.23 mMol) 4-chloromethyl-N-(7-cyclohexyl-4-methoxy-benzothiazol-2-yl)-benzamide in 1 ml THF were added 0.16 g (1.83 mMol) N-(2-methoxyethyl)-methyl amine. The reaction mixture was heated to 70° C. for 2 h. The solvent was evaporated to dryness, the residue taken up in ethyl acetate and washed with water and brine. The organic phase was dried over sodium sulfate and evaporated to dryness in vacuo. The residue was subjected to column chromatography (dichloro methane/methanol 19:1) to yield (0.087 g (81%) of N-(7-cyclohexyl-4-methoxy-benzothiazol-2-yl)-4-{[(2-methoxy-ethyl)-methyl-amino]-methyl}-benzamide as a light yellow foam. ES-MS m/e (%): 468 ([M+H]$^+$, 100).

EXAMPLE 25

N-(7-Cyclohexyl-4-methoxy-benzothiazol-2-yl)-2-pyrrolidin-1-yl-methyl-isonicotinamide a) 2-Chloromethyl-N-(7-cyclohexyl-4-methoxy-benzothiazol-2-yl)-isonicotinamide To a solution of 0.195 g (1.0 mMol) 7-cyclohexyl-4-methoxy-benzothiazol-2-yl-amine in 5 ml THF were added 0.15 ml ethyl diisopropyl amine and 0.2 g (1.20 mMol) 4-(2-chloromethyl)-isonicotinic acid chloride, dissolved in 5 ml of THF. The reaction mixture was stirred at 70° C. for 16 h. The solvent was evaporated to dryness, the residue taken up in dichloro methane and washed with water and brine. The organic phase was dried over sodium sulfate and evaporated to dryness in vacuo. The residue was subjected to column chromatography (dichloro methane/methanol 40:1) to yield 0.137 g (35%) of 2-chloromethyl-N-(7-cyclohexyl-4-methoxy-benzothiazol-2-yl)-isonicotinamide as a dark brown solid. ES-MS m/e (%): 416 ([M+H]$^+$, 100).

b) N-(7-Cyclohexyl-4-methoxy-benzothiazol-2-yl)-2-pyrrolidin-1-ylmethyl-isonicotinamide To a solution of 0.13 g (0.31 mMol) 2-chloromethyl-N-(7-cyclohexyl-4-methoxy-benzothiazol-2-yl)-isonicotinamide in 1 ml THF were added 0.1 ml (1.3 mMol) pyrrolidine. The reaction mixture was heated to 70° C. for 3 h. The solvent was evaporated to dryness, the residue taken up in dichloro methane and washed with water and brine. The organic phase was dried over sodium sulfate and evaporated to dryness in vacuo. The residue was subjected to column chromatography (dichloro methane/methanol 19:1->9:1) and subsequent crystallization from methanol/ethyl acetate/diethyl ether afforded 0.026 g (18%) of N-(7-cyclohexyl-4-methoxy-benzothiazol-2-yl)-2-pyrrolidin-1-yl-methyl-isonicotinamide as a yellow solid. ES-MS m/e (%): 451 ([M+H]$^+$, 100).

EXAMPLE 26

Morpholine-4-carboxylic acid (4-methoxy-7-piperidin-4-yl-benzothiazol-2-yl)-amide hydrochloride 4-{4-Methoxy-2-[(morpholine-4-carbonyl)-amino]-benzothiazol-7-yl}-piperidine-1-carboxylic acid tert-butyl ester To a solution of 0.13 g (0.274 mMol) of 4-{4-Methoxy-2-[(morpholine-4-carbonyl)-amino]-benzothiazol-7-yl}-3,6-dihydro-2H-pyridine-1-carboxylic acid tert-butyl ester in 6.0 ml of methanol and 6.0 ml of tetrahydrofuran 80.0 mg of Pd/C (10%) were added. The reaction mixture was hydrogenated at 60° C. for 8 h, then filtered and evaporated to dryness. The residue was subjected to column chromatography on silica gel (ethyl acetate) to yield 0.048 g (37%) 4-{4-Methoxy-2-[(morpholine-4-carbonyl)-amino]-benzothiazol-7-yl}-piperidine-1-carboxylic acid tert-butyl ester as a colorless foam. ES-MS m/e (%): 477 ([M+H]$^+$, 100).

Morpholine-4-carboxylic acid (4-methoxy-7-piperidin-4-yl-benzothiazol-2-yl)-amide hydrochloride (1:1)

0.45 g (0.094 mMol) 4-{4-Methoxy-2-[(morpholine-4-carbonyl)-amino]-benzothiazol-7-yl}-piperidine-1-carboxylic acid tert-butyl ester were dissolved in 2 ml 2.5 M HCl/MeOH and heated to reflux for 1.5 h. The reaction mixture was concentrated in vacuo and taken up in 5 ml isopropanol. The suspension formed was filtered and the material on the filter was washed with diethyl ether and dried in vacuo. One obtained 26 mg (67%) morpholine-4-carboxylic acid (4-methoxy-7-piperidin-4-yl-benzothiazol-2-yl)-amide hydrochloride (1:1) as a white solid. F.p.: 314–315° C.

EXAMPLE 27

N-(4-Methoxy-7-piperidin-4-yl-benzothiazol-2-yl)-2-methyl-isonicotinamide hydrochloride 4-{4-Methoxy-2-[(2-methyl-pyridine-4-carbonyl)-amino]-benzothiazol-7-yl}-3,6-dihydro-2H-pyridine-1-carboxylic acid tert-butyl ester To a solution of 0.35 g (0.97 mMol) 4-(2-amino-4-methoxy-benzothiazol-7-yl)-3,6-dihydro-2H-pyridine-1-carboxylic acid tert-butyl ester in 20 ml THF were added 0.365 ml ethyl diisopropyl amine and 0.2 g (1.10 mMol) 4-(2-chloromethyl)-isonicotinic acid chloride, dissolved in 10 ml dichloro methane. The reaction mixture was stirred at room temperature for 72 h. Then 5 ml methanol were added. The solvent was evaporated to dryness, the residue taken up in dichloro methane and washed with water and brine. The organic phase was dried over sodium sulfate and evaporated to dryness in vacuo. The residue was subjected to column chromatography (ethyl acetate) to yield 0.32 g (69%) of 4-{4-methoxy-2-[(2-methyl-pyridine-4-carbonyl)-amino]-benzothiazol-7-yl}-3,6-dihydro-2H-pyridine-1-carboxylic acid tert-butyl ester as a dark brown solid. ES-MS m/e (%): 481 ([M+H]$^+$, 100).

4-[4-Methoxy-2-[(2-methyl-pyridine-4-carbonyl)-amino]-benzothiazol-7-yl]-piperidine-1-carboxylic acid tert-butyl ester To a solution of 0.30 g (0.62 mMol) of 4-{4-methoxy-2-[(2-methyl-pyridine-4-carbonyl)-amino]-benzothiazol-7-yl}-3,6-dihydro-2H-pyridine-1-carboxylic acid tert-butyl ester in 15.0 ml of methanol and 15.0 ml THF 160.0 mg of Pd/C (10%) were added. The reaction mixture was hydrogenated at 60° C. for 10 h, then filtered and evaporated to dryness in vacuo. The residue was triturated in diethyl ether to yield 0.15 g (53%) 4-{4-methoxy-2-[(2-methyl-pyridine-4-carbonyl)-amino]-benzothiazol-7-yl}-piperidine-1-carboxylic acid tert-butyl ester as a white solid. F.p.: 155–157° C.

N-(4-Methoxy-7-piperidin-4-yl-benzothiazol-2-yl)-2-methyl-isonicotinamide hydrochloride (1:2)

0.15 g (0.31 mMol) 4-{4-methoxy-2-[(2-methyl-pyridine-4-carbonyl)-amino]-benzothiazol-7-yl}-piperidine-1-carboxylic acid tert-butyl ester were dissolved in 4 ml 2.5 M HCl/MeOH and heated to reflux for 1.5 h. The reaction mixture was concentrated in vacuo and taken up in 5 ml isopropanol. The suspension formed was filtered and the material on the filter was washed with diethyl ether and dried in vacuo. One obtained 80 mg (57%) N-(4-methoxy-7-piperdin-4-yl-benzothiazol-2-yl)-2-methyl-isonicotinamide hydrochloride (1:2) as a white solid. F.p.: 272–277° C.

Analogously to Example 3 there was obtained:

EXAMPLE 28

N-[4-Methoxy-7-(tetrahydro-pyran-4-yl)-benzothiazol-2-yl]-6-methyl-nicotinamide

From 6-methylnicotinic acid, HATU and N-diethylisopropylamine in THF, then treatment with 4-methoxy-7-(tetrahydro-pyran-4-yl)-benzothiazol-2-ylamine in dioxane and DMF. ES-MS m/e (%): 384 (M+H$^+$, 100).

EXAMPLE 29

4-[2-(4-Fluoro-benzoylamino)-4-methoxy-benzothiazol-7-yl]-piperidine-1-carboxylic acid methyl ester To a suspension of 0.1 g (0.24 mMol) 4-fluoro-N-[4-methoxy-7-piperidine-4-yl-benzothiazol-2-yl]-benzamide hydrochloride (1:1) in 3 ml THF were added 0.036 ml triethyl amine. At 0° C. 0.020 ml (0.26 mMol) chloro formic acid methyl ester was added dropwise and stirred for 1 h. Then a mixture of 5 ml sat. aqueous sodium bicarbonate and 10 ml water were added. This was extracted three times with 15 ml ethyl acetate, the combined organic phase were dried over sodium sulfate and evaporated to dryness in vacuo. One obtained 0.080 g (76%) 4-[2-(4-fluoro-benzoylamino)-4-methoxy-benzothiazol-7-yl]-piperidine-1-carboxylic acid methyl ester as a white solid. F.p.: 238–239° C.

EXAMPLE 30

4-{4-Methoxy-2-[(morpholine-4-carbonyl)-amino]-benzothiazol-7-yl}-piperidine-1-carboxylic acid methyl ester To a suspension of 0.05 g (0.12 mMol) morpholine-4-carboxylic acid (4-methoxy-7-piperidin-4-yl-benzothiazol- 2-yl)-amide hydrochloride (1:1) in 3 ml THF were added 0.019 ml triethyl amine. At 0° C. 0.011 ml (0.13 mMol) chloro formic acid methyl ester was added dropwise and stirred for 1 h. Then a mixture of 5 ml sat. aqueous sodium bicarbonate and 10 ml water were added. This was extracted three times with 15 ml ethyl acetate, the combined organic phase were dried over sodium sulfate and evaporated to dryness in vacuo. One obtained 0.037 g (70%) 4-{4-methoxy-2-[(morpholine-4-carbonyl)-amino]-benzothiazol-7-yl}-piperidine-1-carboxylic acid methyl ester as a white solid. F.p.: 179–185° C.

EXAMPLE 31

2-Methoxy-N-[4-methoxy-7-(tetrahydro-pyran-4-yl)-benzothiazol-2-yl]-isonicotinamide To a stirred solution of 0.09 ml (2.23 mmol) methanol in 5 ml dioxane at room temperature was added 49 mg (1.12 mmol) sodium hydride (55% dispersion in mineral oil) and the mixture heated at 50° C. for 1 hour. 100 mg (0.22 mmol) 2-bromo-N-[4-methoxy-7-(tetrahydro-pyran-4-yl)-benzothiazol-2-yl]-isonicotinamide was then added and the mixture heated at 50° C. for 16 h. The reaction mixture was then cooled to room temperature and poured onto water. The mixture was extracted three times with dichloromethane, and the combined organic phases were dried over sodium sulfate and concentrated in vacuo. Flash chromatography (ethyl acetate) followed by trituration in ether and hexane afforded 60 mg (67%) 2-methoxy-N-[4-methoxy-7-(tetrahydro-pyran-4-yl)-benzothiazol-2-yl]-isonicotinamide as a white crystalline solid. ES-MS m/e (%): 398 ([M−H]−, 100).

In an analogous manner there was obtained:

EXAMPLE 32

2-Ethoxy-N-[4-methoxy-7-(tetrahydro-pyran-4-yl)-benzothiazol-2-yl]-isonicotinamide From 2-bromo-N-[4-methoxy-7-(tetrahydro-pyran-4-yl)-benzothiazol-2-yl]-isonicotinamide with sodium hydride and ethanol in dioxane and DMF. ES-MS m/e (%): 414 (M+H+, 100).

EXAMPLE 33

2-Ethyl-N-[4-methoxy-7-(tetrahydro-pyran-4-yl)-benzothiazol-2-yl]-isonicotinamide
a) N-[4-Methoxy-7-(tetrahydro-pyran-4-yl)-benzothiazol-2-yl-2-vinyl-isonicotinamide To a stirred solution of 200 mg (0.45 mmol) 2-bromo-N-[4-methoxy-7-(tetrahydro-pyran-4-yl)-benzothiazol-2-yl]-isonicotinamide in 10 ml DMF were added 283 mg (0.89 mmol) vinyltri-n-butyltin, 38 mg (0.05 mmol) bis(triphenylphosphine)palladium(II) chloride, 70 mg (0.27 mmol) triphenylphosphine, 151 mg (3.57 mmol) lithium chloride and 10 mg (0.04 mmol) 2,6-di-tert-butyl-para-cresol. The mixture was heated at 100° C. for 48 h and then poured onto water and extracted three times with dichloromethane. The combined organic phases were dried over sodium sulfate and concentrated in vacuo. Flash chromatography (hexane then 1/1 ethyl acetate/hexane) followed by trituration in hexane/dichloromethane afforded 100 mg (57%) N-[4-methoxy-7-(tetrahydro-pyran-4-yl)-benzothiazol-2-yl]-2-vinyl-isonicotinamide as a white crystalline solid. ES-MS m/e (%): 396 (M+H+, 100).
b) 2-Ethyl-N-[4-methoxy-7-(tetrahydro-pyran-4-yl)-benzothiazol-2-yl]-isonicotinamide To a stirred solution of 90 mg (0.23 mmol) N-[4-methoxy-7-(tetrahydro-pyran-4-yl)-benzothiazol-2-yl]-2-vinyl-isonicotinamide in 10 ml methanol and 10 ml dichloromethane was added a spatula end of 10% palladium on charcoal and the mixture was then stirred for 16 h at room temperature under an atmosphere of hydrogen. The mixture was then filtered, washing with dichloromethane, and the filtrate concentrated in vacuo and triturated in ether to afford 80 mg (88%) 2-ethyl-N-[4-methoxy-7-(tetrahydro-pyran-4-yl)-benzothiazol-2-yl]-isonicotinamide as a yellow solid. ES-MS m/e (%): 398 (M+H+, 100).

In an analogous manner there was obtained:

EXAMPLE 34

N-[4-Methoxy-7-(tetrahydro-pyran-4-yl)-benzothiazol-2-yl]-2-propyl-isonicotinamide From 2-bromo-N-[4-methoxy-7-(tetrahydro-pyran-4-yl)-benzothiazol-2-yl]-isonicotinamide with allyltri-n-butyltin, bis(triphenylphosphine)palladium(II) chloride, triphenylphosphine, lithium chloride and 2,6-di-tert-butyl-para-cresol in DMF, then hydrogenation with palladium on charcoal in dichloromethane and methanol. ES-MS m/e (%): 412 (M+H+, 100).

Analogously to Example 31 there was obtained:

EXAMPLE 35

2-Isopropoxy-N-[4-methoxy-7-(tetrahydro-pyran-4-yl)-benzothiazol-2-yl]-isonicotinamide From 2-bromo-N-[4-methoxy-7-(tetrahydro-pyran-4-yl)-benzothiazol-2-yl]-isonicotinamide with sodium hydride and isopropanol in dioxane and DMF. ES-MS m/e (%): 414 (M+H+, 100).

Analogously to Example 33 there was obtained:

EXAMPLE 36

2-Isopropyl-N-[4-methoxy-7-(tetrahydro-pyran-4-yl)-benzothiazol-2-yl]-isonicotinamide From 2-bromo-N-[4-methoxy-7-(tetrahydro-pyran-4-yl)-benzothiazol-2-yl]-isonicotinamide with isoprenyltri-n-butyltin, bis(triphenylphosphine)palladium(II) chloride, triphenylphosphine, lithium chloride and 2,6-di-tert-butyl-para-cresol in DMF, then hydrogenation with palladium on charcoal in dichloromethane and methanol. ES-MS m/e (%): 412 (M+H+, 100).

Analogously to Example 1 there was obtained:

EXAMPLE 37

[7-(5,6-Dihydro-4H-pyran-2-yl)-4-methoxy-benzothiazol-2-yl]-carbamic acid methyl ester From (7-iodo-4-methoxy-benzothiazol-2-yl)-carbamic acid methyl ester with tributyl-(5,6-dihydro-4H-pyran-2-yl)-stannane, bis(dibenzylideneacetone)palladium, trifurylphosphine and triethylamine in dioxane. ES-MS m/e (%): 321 (M+H+, 100).

Analogously to Example 2 there was obtained:

EXAMPLE 38

[4-Methoxy-7-(tetrahydro-pyran-2-yl)-benzothiazol-2-yl]-carbamic acid methyl ester From [7-(5,6-dihydro-4H-pyran-2-yl)-4-methoxy-benzothiazol-2-yl]-carbamic acid methyl ester by hydroge-

EXAMPLE 39

2-Bromo-N-[4-methoxy-7-(tetrahydro-pyran-2-yl)-
benzothiazol-2-yl]-isonicotinamide a) 4-Methoxy-7-(tetrahydro-pyran-2-yl)-benzothiazol-2-ylamine To a solution of 2.60 g (8.06 mmol) [4-methoxy-7-(tetrahydro-pyran-2-yl)-benzothiazol-2-yl]-carbamic acid methyl ester in 100 ml ethylene glycol was added 100 ml 2 N NaOH and the mixture was heated at 100° C. for 3 h. After cooling to room, the reaction mixture was poured into water and extracted three times with dichloromethane. The combined organic phases were dried over sodium sulfate and concentrated in vacuo. Flash chromatography (acetone/hexane 1/4–1/2) afforded 1.70 g (80%) 4-methoxy-7-(tetrahydro-pyran-2-yl)-benzothiazol-2-ylamine as a white solid. ES-MS m/e (%): 265 (M+H$^+$, 100).

b) 2-Bromo-N-[4-methoxy-7-(tetrahydro-pyran-2-yl)-benzothiazol-2-yl]-isonicotinamide To a stirred solution of 0.99 g (4.92 mmol) 2-bromo-isonicotinic acid in 40 ml THF were added 2.16 g (5.67 mmol) HATU and 0.97 ml (5.67 mmol) N-ethyldiisopropylamine and stirring continued at room temperature for 1 h. A solution of 1.00 g (3.78 mmol) 4-methoxy-7-(tetrahydro-pyran-2-yl)-benzothiazol-2-ylamine in 20 ml dioxane and 4 ml DMF was then added and stirring continued at room temperature for 48 h. The reaction mixture was then poured into aqueous sodium bicarbonate solution and extracted three times with dichloromethane. The combined organic phases were washed with 1 M hydrochloric acid, then dried over sodium sulfate and concentrated in vacuo. Flash chromatography (acetone/hexane 1/4) followed by trituration in ether afforded 500 mg (29%) 2-bromo-N-[4-methoxy-7-(tetrahydro-pyran-2-yl)-benzothiazol-2-yl]-isonicotinamide as a light yellow crystalline solid. ES-MS m/e (%): 450 (M$\{^{81}Br\}$+H$^+$, 100), 448 (M$\{^{79}Br\}$+H$^+$, 80).

In an analogous manner there were obtained:

EXAMPLE 40

4-Fluoro-N-[4-methoxy-7-(tetrahydro-pyran-2-yl)-
benzothiazol-2-yl]-benzamide

From 4-fluorobenzoic acid, HATU and N-diethylisopropylamine in THF, then treatment with 4-methoxy-7-(tetrahydro-pyran-2-yl)-benzothiazol-2-ylamine in dioxane and DMF. ES-MS m/e (%): 387 (M+H$^+$, 100).

EXAMPLE 41

N-[4-Methoxy-7-(tetrahydro-pyran-2-yl)-
benzothiazol-2-yl]-2-methyl-isonicotinamide From 2-methyl-isonicotinic acid hydrochloride, HATU and N-diethylisopropylamine in THF, then treatment with 4-methoxy-7-(tetrahydro-pyran-2-yl)-benzothiazol-2-ylamine in dioxane and DMF. ES-MS m/e (%): 384 (M+H$^+$, 100).

Analogously to Example 6 there was obtained:

EXAMPLE 42

N-[4-Methoxy-7-(tetrahydro-pyran-2-yl)-
benzothiazol-2-yl]-2-morpholin-4-yl-
isonicotinamide From 2-bromo-N-[4-methoxy-7-(tetrahydro-pyran-2-yl)-benzothiazol-2-yl]-isonicotinamide with cesium carbonate and morpholine in NMP. ES-MS m/e (%): 455 (M+H$^+$, 100).

EXAMPLE 43

N-[4-Methoxy-7-(tetrahydro-pyran-4-yl)-
benzothiazol-2-yl]-2-pyrrolidin-1-ylmethyl-
isonicotinamide The title compound was prepared from 2-chloromethyl-N-[7-(tetrahydro-pyran-4-yl)-4-methoxy-benzothiazol-2-yl]-isonicotinamide (prepared from 4-methoxy-7-(tetrahydro-pyran-4-yl)-benzothiazol-2-ylamine and 4-(2-chloromethyl)-isonicotinic acid chloride as described for 2-chloromethyl-N-(7-cyclohexyl-4-methoxy-benzothiazol-2-yl)-isonicotinamide) and pyrrolidine as described for N-(7-Cyclohexyl-4-methoxy-benzothiazol-2-yl)-2-pyrrolidin-1-ylmethyl-isonicotinamide and obtained as light yellow solid (62% yield), mp 200–202° C. MS: m/e=453 (M+H+).

EXAMPLE 44

Morpholine-4-carboxylic acid [4-methoxy-7-
(tetrahydro-pyran-4-yl)-benzothiazol-2-yl]-amide To a solution of 4-methoxy-7-(tetrahydro-pyran-4-yl)-benzothiazol-2-ylamine (265 mg, 1.0 mmol) in dichloromethane (15 ml) is subsequently added pyridine (0.24 ml, 3.0 mmol) and phenyl chloroformate (0.5 ml, 1.2 mmol) and the resulting solution stirred for 45 min at ambient temperature. Then morpholine (313 mg, 3.6 mmol) is added and the mixture stirred at ambient temperature for 15 min and at 40° C. for 2.5 h. After cooling to ambient temperature, saturated aqueous sodium carbonate (15 ml) is added, the organic phase is separated, dried and the solvent evaporated in vacuo. Flash chromatography (silica, eluent: dichloromethane containing methanol (gradient from 0 to 5%)) afforded the title compound as white crystals (21% yield), mp 217–220° C. MS: m/e=378 (M+H$^+$).

Following the method of example 44 the compound of example 45 was prepared.

EXAMPLE 45

4-Hydroxy-piperidine-1-carboxylic acid [4-
methoxy-7-(tetrahydro-pyran-4-yl)-benzothiazol-2-
yl]-amide Using 4-hydroxy-piperidine the title compound was prepared as a light yellow solid (80% yield), mp 106–109° C. MS: m/e=392 (M+H$^+$).

Analogously to Example 6 there were obtained

EXAMPLE 46

2-(2-Methoxy-ethylamino)-N-[4-methoxy-7-
(tetrahydro-pyran-4-yl)-benzothiazol-2-yl]-
isonicotinamide From 2-bromo-N-[4-methoxy-7-(tetrahydro-pyran-4-yl)-benzothiazol-2-yl]-isonicotinamide with cesium carbonate and 2-methoxyethylamine. ES-MS m/e (%): 443 (M+H$^+$, 100).

EXAMPLE 47

2-[(2-Methoxy-ethyl)-methyl-amino]-N-[4-methoxy-
7-(tetrahydro-pyran-4-yl)-benzothiazol-2-yl]-
isonicotinamide From 2-bromo-N-[4-methoxy-7-(tetrahydro-pyran-4-yl)-benzothiazol-2-yl]-isonicotinamide with cesium carbonate and N-(2-methoxyethyl)methylamine. ES-MS m/e (%): 457 (M+H$^+$, 100).

We claim:
1. A compound of the formula I

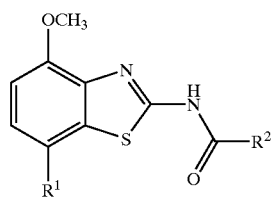

wherein
R¹ is 3,6-dihydro-2H-pyran-4-yl, 5,6-dihydro-4H-pyran-3-yl, 5,6-dihydro-4H-pyran-2-yl, tetrahydropyran-2,3 or 4-yl, cyclohex-1-enyl, cyclohexyl, substituted or unsubstitited 1,2,3,6-tetrahydro-pyridin-4-yl or substituted or unsubstituted piperidin-4-yl, wherein when R1 is substituted, the substituent is —C(O)CH₃ or —C(O)OCH₃ in the 1-position of the N-atom;
R² is lower alkyl, piperidin-1-yl, piperidin-1-yl substituted by hydroxy, phenyl, phenyl substituted by —(CH₂)ₙ—N(R')—C(O)—(CH₂)ₙ—NR'₂, —(CH₂)ₙ-halogen) lower alkyl or —(CH₂)ₙ—N(R')—(CH₂)ₙ—O-lower alkyl, morpholinyl, pyridinyl, or pyridinyl substituted by halogen, —N(R')—(CH₂)ₙ—O-lower alkyl, lower alkyl, lower alkoxy, morpholinyl or —(CH₂)ₙ-pyrrolidinyl;
n is 0, 1 or 2;
R' is hydrogen or lower alkyl;
and pharmaceutically acceptable acid addition salts thereof.

2. The compound according to claim 1, wherein R¹ is 3,6-dihydro-2H-pyran-4-yl.

3. The compound according to claim 2, wherein the compound is [7-(3,6-dihydro-2H-pyran-4-yl)-4-methoxy-benzothiazol-2-yl]-carbamic acid methyl ester.

4. The compound according to claim 1, wherein R¹ is tetrahydropyran-4-yl.

5. The compound according to claim 4, wherein the compound is selected from the group consisting of:
4-fluoro-N-[4-methoxy-7-(tetrahydro-pyran-4-yl)-benzothiazol-2-yl]-benzamide,
N-[4-methoxy-7-(tetrahydro-pyran-4-yl)-benzothiazol-2-yl]-6-methyl-nicotinamide,
2-methoxy-N-[4-methoxy-7-(tetrahydro-pyran-4-yl)-benzothiazol-2-yl]-isonicotinamide,
2-ethoxy-N-[4-methoxy-7-(tetrahydro-pyran-4-yl)-benzothiazol-2-yl]-isonicotinamide,
2-ethyl-N-[4-methoxy-7-(tetrahydro-pyran-4-yl)-benzothiazol-2-yl]-isonicotinamide
N-[4-methoxy-7-(tetrahydro-pyran-4-yl)-benzothiazol-2-yl]-2-propyl-isonicotinamide,
2-isopropoxy-N-[4-methoxy-7-(tetrahydro-pyran-4-yl)-benzothiazol-2-yl]-isonicotinamide,
2-isopropyl-N-[4-methoxy-7-(tetrahydro-pyran-4-yl)-benzothiazol-2-yl]-isonicotinamide,
N-[4-methoxy-7-(tetrahydro-pyran-4-yl)-benzothiazol-2-yl]-2-pyrrolidin-1-ylmethyl-isonicotinamide,
morpholine-4-carboxylic acid [4-methoxy-7-(tetrahydro-pyran-4-yl)-benzothiazol-2-yl]-amide,
4-hydroxy-piperidine-1-carboxylic acid [4-methoxy-7-(tetrahydro-pyran-4-yl)-benzothiazol-2-yl]-amide,
2-(2-methoxy-ethylamino)-N-[4-methoxy-7-(tetrahydro-pyran-4-yl)-benzothiazol-2-yl]-isonicotinamide and
2-[(2-methoxy-ethyl)-methyl-amino]-N-[4-methoxy-7-(tetrahydro-pyran-4-yl)-benzothiazol-2-yl]-isonicotinamide.

6. The compound according to claim 1, wherein R¹ is tetrahydropyran-2-yl.

7. The compound according to claim 6, wherein the compound is selected from the (group consisting of:
2-bromo-N-[4-methoxy-7-(tetrahydro-pyran-2-yl)-benzothiazol-2-yl]-isonicotinamide,
4-fluoro-N-[4-methoxy-7-(tetrahydro-pyran-2-yl)-benzothiazol-2-yl]-benzamide,
N-[4-methoxy-7-(tetrahydro-pyran-2-yl)-benzothiazol-2-yl]-2-methyl-isonicotinamide and
N-[4-methoxy-7-(tetrahydro-pyran-2-yl)-benzothiazol-2-yl]-2-morpholin-4-yl-isonicotinamide.

8. The compound according to claim 1, wherein R¹ is 1,2,3,6-tetrahydro-pyridin-4-yl, substituted by —C(O)CH₃ in the 1-position of the N-atom.

9. The compound according to claim 8, wherein the compound is N-[7-(1-acetyl-1,2,3,6-tetrahydro-pyridin-4-yl)-4-methoxy-benzothiazol-2-yl]-4-fluoro-benzamide.

10. The compound according to claim 1, wherein R¹ is piperidin-4-yl, substituted on the N-atom by —C(O)CH₃.

11. The compound according to claim 10, wherein the compound is selected from the group consisting of:
N-[7-(1-acetyl-piperidin-4-yl)-4-methoxy-benzothiazol-2-yl]-4-fluoro-benzamide, morpholine-4-carboxylic acid [7-(1-acetyl-piperidin-4-yl)-4-methoxy-benzothiazol-2-yl]-amide,
N-[7-(1-acetyl-piperidin-4-yl)-4-methoxy-benzothiazol-2-yl]-2-methyl-isonicotinamide,
N-[7-(1-acetyl-piperidin-4-yl)-4-methoxy-benzothiazol-2-yl]-4-{[(2-methoxy-ethyl)-methylamino]-methyl}-benzamide,
N-[7-(1-acetyl-piperidin-4-yl)-4-methoxy-benzothiazol-2-yl]-4-methyl-benzamide,
N-[7-(1-acetyl-piperidin-4-yl)-4-methoxy-benzothiazol-2-yl]-2-morpholin-4-yl-isonicotinamide and
N-[7-(]-acetyl-piperidin-4-yl)-4-methoxy-benzothiazol-2-yl]-2-methoxy-isonicotinamide.

12. The compound according to claim 1, wherein R¹ is cyclohex-1-enyl.

13. The compound according to claim 12, wherein the compound is (7-cyclohex-1-enyl-4-methoxy-benzothiazol-2-yl)-carbamic acid methyl ester.

14. The compound according to claim 1, wherein R¹ is cyclohexyl.

15. The compound according to claim 14, wherein the compound is selected from the group consisting of:
N-(7-cyclohexyl-4-methoxy-benzothiazol-2-yl)-4-fluoro-benzamide,
N-(7-cyclohexyl-4-methoxy-benzothiazol-2-yl)-4-{[(2-methoxy-ethyl)-methyl-amino]-methyl}-benzamide and
N-(7-cyclohexyl-4-methoxy-benzothiazol-2-yl)-2-pyrrolidin-1-yl-methyl-isonicotinamide.

16. A process for preparing a compound of formula I as defined in claim 1, which process comprises
reacting a compound of formula

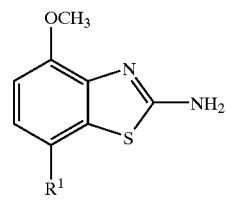

(6)

with a compound of formula

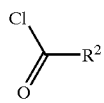 (7)

or with a compound of formula

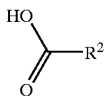 (8)

to yield a compound of formula

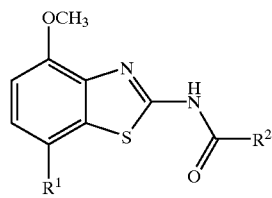 I wherein $R^1$ and $R^2$ are as defined in claim 1; and optionally converting the compounds obtained into pharmaceutically acceptable acid addition salts.

17. A process for preparing a compound of formula I as defined in claim 1, which process comprises:

hydrogenating a compound of formula

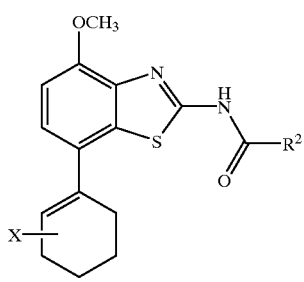 I-4 to yield a compound of formula

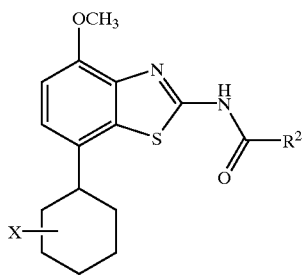 I-5 wherein X is a ring atom selected from the group consisting of O, N or C, which may be in different ring positions, and wherein when the ring atom is N, said N may be substituted by —C(O)CH$_3$ or —C(O)OCH$_3$; and optionally converting the compounds obtained into pharmaceutically acceptable acid addition salts.

18. A process for preparing a compound of formula I as defined in claim 1, which process comprises:

reacting a compound of formula

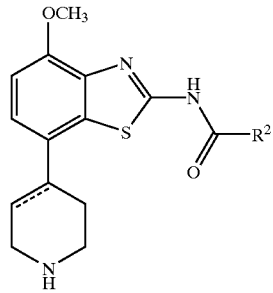 I-3 with Ac$_2$O to yield a compound of formula

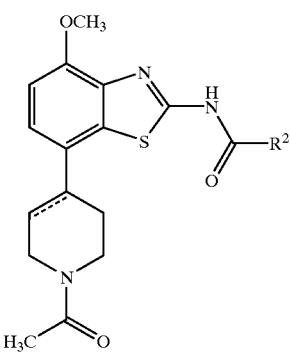 I-5 wherein the dotted line indicated the presence of absence of a bond and $R^2$ is as described in claim 1; and optionally converting the compounds obtained into pharmaceutically acceptable acid addition salts.

19. A method of treating a disease mediated by the adenosine receptor comprising administering to a patient in need of such treatment, an effective amount of a compound of the formula I

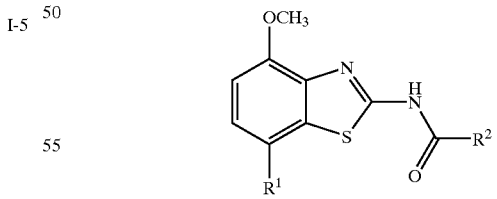 I wherein $R^1$ is 3,6-dihydro-2H-pyran-4-yl, 5,6-dihydro-4H-pyran-3-yl, 5,6-dihydro-4H-pyran-2-yl, tetrahydropyran-2,3 or 4-yl, cyclohex-1-enyl, cyclohexyl, substituted or unsubstituted 1,2,3,6-tetrahydro-pyridin-4-yl or substituted or unsubstituted piperidin-4-yl, wherein when R1 is substituted, the substituent is —C(O)CH$_3$ or —C(O)OCH$_3$ in the 1-position of the N-atom;

R² is lower alkyl, piperidin-1-yl, piperidin-1-yl substituted by hydroxy, phenyl, phenyl substituted by —(CH₂)ₙ—N(R')—C(O)—(CH₂)ₙ—NR'₂, —(CH₂)ₙ-halogen, lower alkyl or —(CH₂)ₙ—N(R')—(CH₂)ₙ—O-lower alkyl, morpholinyl, pyridinyl, or pyridinyl substituted by halogen, —N(R')—(CH₂)ₙ—O-lower alkyl, lower alkyl, lower alkoxy, morpholinyl or —(CH₂)ₙ-pyrrolidinyl;

n is 0, 1 or 2;

R' is hydrogen or lower alkyl;

and pharmaceutically acceptable acid addition salts thereof.

20. The method according to claim 19, wherein said disease is selected from at least one of Alzheimer's disease, Parkinson's disease, Huntington's disease, neuroprotection, schizophrenia, anxiety, pain, respiration deficits, depression, drug addiction, asthma, allergic responses, hypoxia, ischaemia, seizure, and attention deficit hyperactivity disorder.

21. The method according to claim 19, wherein said adenosine receptor is the A₂ₐ receptor.

22. The method according to claim 21, wherein said disease is selected from the group consisting of Alzheimer's disease, depression, drug addiction, neuroprotection, Parkinson's disease, and attention deficit hyperactivity disorder.

23. A pharmaceutical composition comprising a pharmaceutically effective amount of a compound of the formula I

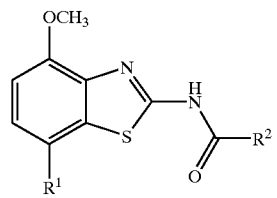

wherein
R¹ is 3,6-dihydro-2H-pyran-4-yl, 5,6-dihydro-4H-pyran-3-yl, 5,6-dihydro-4H-pyran-2-yl, tetrahydropyran-2,3 or 4-yl, cyclohex-1-enyl, cyclohexyl, substituted or unsubstituted 1,2,3,6-tetrahydro-pyridin-4-yl or substituted or unsubstituted piperidin-4-yl, wherein when R1 is substituted, the substituent is —C(O)CH₃ or —C(O)OCH₃ in the 1-position of the N-atom;

R² is lower alkyl, piperidin-1-yl, piperidin-1-yl substituted by hydroxy, phenyl, phenyl substituted by —(CH₂)ₙ—N(R')—C(O)—(CH₂)ₙ—NR'₂, —(CH₂)ₙ-halogen, lower alkyl or —(CH₂)ₙ—N(R')—(CH₂)ₙ—O-lower alkyl, morpholinyl, pyridinyl, or pyridinyl substituted by halogen, —N(R')—(CH₂)ₙ—O-lower alkyl, lower alkyl, lower alkoxy, morpholinyl or —(CH₂)ₙ-pyrrolidinyl;

n is 0, 1 or 2;

R' is hydrogen or lower alkyl;

and pharmaceutically acceptable acid addition salts thereof; and a pharmaceutically acceptable carrier.

* * * * *

UNITED STATES PATENT AND TRADEMARK OFFICE
CERTIFICATE OF CORRECTION

PATENT NO. : 6,734,179 B2
DATED : May 11, 2004
INVENTOR(S) : Alexander Flohr et al.

It is certified that error appears in the above-identified patent and that said Letters Patent is hereby corrected as shown below:

Column 37,
Line 24, delete "halogen) lower alkyl or $-(CH_2)_n-N(R')-(CH_2)_n-$" and insert -- halogen, lower alkyl or $-(CH_2)_n-N(R')-(CH_2)_n-$ --.

Column 41,
Line 22, delete "adenosine receptor is the $A_{2A}$ receptor." and insert -- adenosine receptor is the $A_{2A}$ receptor. --

Signed and Sealed this

Thirtieth Day of November, 2004

JON W. DUDAS
*Director of the United States Patent and Trademark Office*